US008846625B2

(12) United States Patent
Drucker et al.

(10) Patent No.: US 8,846,625 B2
(45) Date of Patent: *Sep. 30, 2014

(54) GLUCAGON-LIKE PEPTIDE-2 ANALOGS

(71) Applicant: NPS Pharmaceuticals, Inc., Bedminster, NJ (US)

(72) Inventors: Daniel J Drucker, Toronto (CA); Anna E. Crivici, Laguna Niguel, CA (US); Martin Sumner-Smith, Palgrave (CA)

(73) Assignee: 1149336 Ontario Inc. (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/794,314

(22) Filed: Mar. 11, 2013

(65) Prior Publication Data

US 2013/0203673 A1    Aug. 8, 2013

Related U.S. Application Data

(60) Division of application No. 12/816,312, filed on Jun. 15, 2010, which is a division of application No. 10/293,941, filed on Nov. 14, 2002, now Pat. No. 7,781,401, which is a continuation of application No. 09/764,070, filed on Jan. 19, 2001, now abandoned, which is a division of application No. 08/835,538, filed on Apr. 8, 1997, now Pat. No. 6,184,201, which is a continuation-in-part of application No. 08/631,273, filed on Apr. 12, 1996, now abandoned, and a continuation-in-part of application No. 08/632,533, filed on Apr. 12, 1996, and a continuation-in-part of application No. 08/422,540, filed on Apr. 14, 1995, now Pat. No. 5,990,077.

(51) Int. Cl.
| C07K 14/00 | (2006.01) |
|---|---|
| A61K 38/16 | (2006.01) |
| A61K 38/26 | (2006.01) |
| A61K 35/37 | (2006.01) |
| C07K 14/605 | (2006.01) |
| G01N 33/483 | (2006.01) |
| A61K 38/00 | (2006.01) |

(52) U.S. Cl.
CPC ............ *A61K 38/26* (2013.01); *C07K 14/605* (2013.01); *A61K 38/00* (2013.01); *G01N 33/4833* (2013.01)
USPC ......... 514/21.3; 514/11.7; 530/324; 530/308; 424/551

(58) Field of Classification Search
None
See application file for complete search history.

(56) References Cited

U.S. PATENT DOCUMENTS

| 4,016,100 A | 4/1977 | Suzuki et al. |
|---|---|---|
| 4,311,712 A | 1/1982 | Evans et al. |
| 4,370,349 A | 1/1983 | Evans et al. |
| 4,372,949 A | 2/1983 | Kodama et al. |
| 4,452,747 A | 6/1984 | Gersonde |
| 4,529,561 A | 7/1985 | Hunt et al. |
| 4,725,442 A | 2/1988 | Haynes |
| 4,737,323 A | 4/1988 | Martin et al. |
| 4,920,016 A | 4/1990 | Allen et al. |
| 4,921,706 A | 5/1990 | Roberts et al. |
| 4,927,637 A | 5/1990 | Morano et al. |
| 4,944,948 A | 7/1990 | Uster et al. |
| 5,008,050 A | 4/1991 | Cullis et al. |
| 5,009,956 A | 4/1991 | Baumann |
| 5,432,156 A | 7/1995 | Matsuno et al. |
| 5,789,379 A | 8/1998 | Drucker et al. |
| 5,834,428 A | 11/1998 | Drucker |
| 5,912,229 A | 6/1999 | Thim et al. |
| 5,990,077 A * | 11/1999 | Drucker .................. 514/7.3 |
| 5,994,500 A * | 11/1999 | Drucker et al. ............... 530/324 |
| 6,051,557 A | 4/2000 | drucker |
| 6,184,201 B1 | 2/2001 | Drucker et al. |
| 6,297,214 B1 | 10/2001 | Drucker |
| 6,489,295 B1 * | 12/2002 | Drucker et al. ............... 514/4.8 |
| 6,586,399 B1 | 7/2003 | Dreucker |
| 7,049,284 B2 | 5/2006 | Drucker |
| 7,176,182 B2 | 2/2007 | Drucker |
| 7,642,241 B2 | 1/2010 | Drucker |
| 7,847,061 B2 | 12/2010 | Sanguenetti |
| 7,960,344 B2 | 6/2011 | Drucker |

FOREIGN PATENT DOCUMENTS

| CA | 2137206 | 6/1995 |
|---|---|---|
| CN | 96194693.8 | 4/1996 |
| EP | 0612531 | 8/1994 |
| WO | WO 8706941 | 11/1987 |
| WO | WO 9318786 | 9/1993 |
| WO | WO 9325579 | 12/1993 |
| WO | WO 9632414 | 10/1996 |
| WO | WO 9731943 | 9/1997 |
| WO | WO 9739031 | 10/1997 |
| WO | WO 9803547 | 1/1998 |
| WO | WO 02066062 | 8/2002 |

OTHER PUBLICATIONS

Wermuth, Pure and Appl. Chem, 1998, 70, 1129-1143.*
Lund, 1983, Journal of biological Chemistry, 258, 3280-3284.*
Mentlein, 1999, Regulatory Peptides, 85, 9-24.*
Barragan, et al., "Changes in arterial blood pressure and heart rate induced by glucagon-like peptide-1-(7-36) amide in rats", American Journal of Physiology, vol. 266, No. 3, part 1, 1994, E459-66.
Benhamou, et al., "Stimulation by recombinant human growth hormone of growth and development of remaining bowel after subtotal ileojejunectomy in rats", J. Pediatric Gastroenterology and Nutrition, vol. 18, No. 4, 1994, 446-452.
Berendsen, et al., "A glimpse of the holy grail?", Scinece, 1998, 282:642-643.
Bloom, "Gut Hormones in adaptation", Gut, 28, S1, 1987, 31-35.
Boismenu, et al., "Modulation of epithelial cell growth by intraepithelial gammadelta T cells", Science, vol. 266, no. 5188, 1994, 1253-1255.
Bongers, et al., "Kinetics of dipeptidyl peptidase IV proteolysis of the growth hormon-releasing factor and analogs", Biochemica Et Biophysica ACTA, vol. 1122, 1992, 147-153.
Boushey, et al., Cancer Research, 61:687-693, 2001.

(Continued)

Primary Examiner — Satyanarayana R Gudibande
(74) Attorney, Agent, or Firm — Stoel Rives LLP

(57) ABSTRACT

Analogs of glucagon-like peptide 2, a product of glucagon gene expression, have been identified as intestinal tissue growth factors. Their formulation as pharmaceutical, and therapeutic use in treating disorders of the small bowel, are described.

13 Claims, No Drawings

(56) References Cited

OTHER PUBLICATIONS

Brubaker, et al., "Regulation of intestinal proglucagon-derived peptide secretion by intestinal regulatory peptides", Endocrinology, vol. 128, No. 6, 1991, 3175-3182.
Brubaker, et al., Am. J. Physiological Society, E1050-E1058, 1997.
Buhl, et al., "Naturally occuring products of proglucagon 111-160 in the porcine and human small intestine", J. Biological Chemistry, vol. 263, No. 18, 1988, 8621-8624.
Calvo, et al., "Structural characterization by affinity cross-linking of glucagon-like peptide-1)7-36) amide receptor in rat brain", J. Neurochemistry, vol. 64, No. 1, 1995, 299-306.
Cameron, et al., Am. J. Physiol. Gastrointent. Liver, Pnysiol. 284:G905-G912, 2003.
Chaet, et al., "Epidermal growth factor enhances intestinal adaptation after massive small bowelresection", J. of Pediatric Surgery, vol. 29, No. 8, 1994, 1035-1039.
Chance, et al., Am. J. Physiological Society, G559-563, 1997.
Cheeseman, et al., "The effect of gastic inhibitory polypeptide and glucagon like peptides on intestinal basolateral membrane hexose transport", American Physiological Society, 1996, APStracts 3:0071G.
Continued Prosecution Application Request filed in U.S. Appl. No. 08/632,533, filed Apr. 16, 2001.
Deacon, et al., "Both subcutaneously and intravanously administered glucagon-like peptide I are rapidly degraded from the NH2-terminus in type II diabetic patients and in healthy subjects", Diabetes, vol. 44, 1995, 1126-1131.
De Miguel, et al., "Trophic effects of neurotensin in massive bowel resection in the rat", Trophic Effects of Neurotensin in Massive Bowel Resection in The Rat, vol. 39, No. 1, 1994, 59-64.
Drucker, et al., "Induction of intestinal epithelial priliferation by glucagon-like peptide 2", Proceedings of the National Academy of Science of USA, vol. 93, No. 15, 1996, 7911-7916.
Drucker, et al., "Regulation of the biological activity of glucagon-like peptide 2 in vivo by dipeptidyl peptidase IV", Nature Biotechnology, vol. 15, 1997, 673-677.
Drucker, et al., "Glucagon and the glucagon-like peptides", Pancreas, vol. 5, No. 4, 1990, 484-488.
Drucker, J. Biological Chemistry, 263, 13475-13478.
Drucker, Am. J. Physiological Society, G79-91, 1999.
Drucker, Gastroenterology, 122:531-544, 2002.
Ehrlich, et al., "Inhibition of pancreatic proglucagon gene expression in mice bearing subcutaneous endocrine tumors", Am. J. Physiology, 1994, E662-E671.
European Search Report issued in EP Application No. 01129072.3 dated Jul. 1, 2002.
European Search Report issued in EP Application No. 08154386.0 dated Nov. 26, 2008.
European Search Report and Written Opinion issued in EP Application No. 08154372.0.
Flint, et al., "Glucagon-like peptide 1 promotes satiety and suppresses energy intake in humans", J. Clin. Invest, vol. 101, No. 3, 1998, 515-520.
Gallwitz, et al., "GLP-1-analogues resistant to degradation by dipeptidyl-peptidase IV in vitro", Reb. Peptides, vol. 86, 2000, 103-111.
Gallwitz, et al., "Structure/activity characterization of glucagon-like peptide-1", Eur. J. Biochem., vol. 225, 1994, 1151-1156.
George, et al., "Molecular forms of glucagon-like peptides in man", FEBS, vol. 192, No. 2, 1985, 275-278.
Goffin, Molecular Endocrinology, 1992, 6, 1381-1392.
Gutzwiller, et al., "Glucagon-like peptide-1: A potent regulator of food intake in humans", GUT, vol. 44, 1999, 81-86.
International Preliminary Examination Report issued in International Application No. PCT/CA1997/00252 dated Jun. 29, 1998.
International Search Report issued in International Patent Application No. PCT/CA1997/00252 dated Sep. 15, 1997.
International Search Report issued in International Patent Application No. PCT/CA1996/00232 dated Sep. 27, 1996.
Interview Summary and Examiner's Amendment issued in U.S. Appl. No. 08/632,533 dated Feb. 16, 2001.
Irwin, et al., "Trout and chicken proglucagon: alternative splicing generates mRNA transcripts encoding glucagon-like peptide 2", Molecular Endocrinology, vol. 9, 1995, 267-277.
Jeppesen, et al., Gastroenterology, 120:806-815, 2001.
Kieffer, et al., "Degradation of glucose-dependent insulinotropic polypeptide and truncated glucagon-like peptide 1 in vitro and in vivo by dipeptidyl peptidase IV", Endocrinology, vol. 136, No. 8, 1995, 3585-3596.
Lee, et al., "Glucagon Gene5'—flanking sequences directed expression of simian virus 40 large T antigen to the intestine, producing carcinoma of the large bowel in transgenic mice", J. Biological Chemistry, vol. 267, No. 15, 1992, 10705-10708.
L'Heureux, et al., J. of Pharmacology and Experimental Therapeutics, 306:347-354, 2003.
Lund, et al., "Regulation of intestinal glucagon gene expression during adaptive growth of small intestine", Digestion, Nov.-Dec. 1993, 371-373.
Madsen, et al., "The dissacociation of tumor-induced weight loss from hypoglycemia in a transplanable pluripotent rat islet tumor results in the segregation of stable alpha-and beta-cell tumor phenotypes", Endocrinology, vol. 133, No. 5, 1993, 2022-2030.
Mentlein, et al., "Dipeptidyl-peptidase IV hydrolyses gastric inhibitory polypeptide, glucagon-like peptide-1(7-36)amide, peptide histidine methionine and is responsible for their degradation in human serum", Eur. J. Biochem., vol. 214, 1993, 829-835.
Mojsov, et al.,"Preproglucagon gene expression in pancreas and intestine diversifies at the level of post-translational processing", J. Biol. Chem. vol. 261, No. 25, 1986, 11880-11889.
Mojsov, et al., "Structural requirements for biological activity of glucagon-like peptide-1" International Journal of Peptide & Protein Research, Sep./Oct. 1992, 333-343.
Mommsen, et al., "Glucagon-like peptides activate hepatic gluconeogenesis", FEBS Letters, vol. 219, No. 1, 1987, 227-232.
Naslund, et al., "Energy intake and appetite are suppressed by glucagon-like peptide-1 (GLP-1) in obese men", Int. J. Obesity, vol. 23, 1999, 304-311.
Nishi, et al., "Cloning for complementary DNAs encoding islet amyloid polypeptide, insulin and glucagon precursors froma new world rodent, the degu, octodon, degus", Mol. Endocrinology, vol. 4, 1990, 1192-1198.
Notice of Allowance and Examiner's Amendment issued in U.S. Appl. No. 08/632,533 dated Jun. 20, 2002.
Notice of Allowance and Examiner's Amendment issued in U.S. Appl. No. 10/293,941 dated Mar. 15, 2010.
Notice of Allowance and Examiner's Amendment issued in U.S. Appl. No. 11/325,527 dated Sep. 27, 2010.
Notice of Allowance and Examiner's Amendment issued in U.S. Appl. No. 12/816,312.
Notice of Appeal filed in U.S. Appl. No. 08/632,533, filed Mar. 4, 1999.
Office Action issued in U.S. Appl. No. 08/835,538 dated Jan. 8, 1998.
Office Action issued in U.S. Appl. No. 08/835,538 dated Sep. 4, 1998.
Office Action (final) issued in U.S. Appl. No. 08/835,538 dated Jun. 7, 1999.
Office Action issued in U.S. Appl. No. 10/293,941 dated Mar. 30, 2007.
Office Action issued in U.S. Appl. No. 10/293,941 dated Sep. 19, 2007.
Office Action issued in U.S. Appl. No. 10/293,941 dated Jul. 18, 2008.
Office Action (final) issued in U.S. Appl. No. 10/293,941 dated Apr. 24, 2009.
Office Action issued in U.S. Appl. No. 08/669,791 dated Jun. 20, 1997.
Office Action issued in U.S. Appl. No. 08/422,540 dated Mar. 27, 1997.
Office Action issued in U.S. Appl. No. 08/422,540 dated Jan. 8, 1998.
Office Action (final) issued in U.S. Appl. No. 08/422,540 dated Sep. 4, 1998.
Office Action issued in U.S. Appl. No. 10/042,746 dated Feb. 14, 2005.

(56) References Cited

OTHER PUBLICATIONS

Office Action issued U.S. Appl. No. 11/325,527 dated May 5, 2009.
Office Action issued U.S. Appl. No. 11/325,527 dated Mar. 4, 2010.
Office Action issued in U.S. Appl. No. 08/632,533 dated Dec. 23, 1997.
Office Action (final) issued in U.S. Appl. No. 08/632,533 dated Sep. 4, 1998.
Office Action issued in U.S. Appl. No. 08/632,533 dated Apr. 27, 2001.
Office Action (final) issued in U.S. Appl. No. 08/632,533 dated Nov. 27, 2001.
Office Action issued in U.S. Appl. No. 12/816,312 dated Jun. 13, 2011.
Office Action issued in U.S. Appl. No. 12/816,312 dated Feb. 14, 2012.
Oguchi, et al., "Profile of IGF-binding proteins secreted by intestinal epithelial cells changes with differentiation", Am. J. of Physiology, vol. 267, No. 5, Pt. 1, 1994, G843-G850.
Orksov, et al., "Glucagon-like peptides GLP-1 and GLP-2, predicted products of the glucagon gene, are secreted separately from pig small intestine but not pancreas", Endocrinology, vol. 119, No. 4, 1986, 1467-1475.
Orksov, et al., "Pancreatic and intestinal processing of proglucagon in man", Diabetologia, vol. 30, 1987, 874-881.
Orksov, et al., "Carboxypeptidase-B-like processing of the C-24, terminus of glucagon-like peptide-2 in pig and human small intestince", FEBS Letters: vol. 247, No. 2, 1989, 193-196.
Orksov, et al., "Radio-immunoassays for glucagon-like peptides 1 and 2 (GLP-1 and GLP-2)", Scand. J. Clin. Lab. Invest; vol. 47, No. 2, 1987, 165-174.
Preliminary Amendment filed in U.S. Appl. No. 10/293,941, filed Apr. 13, 2004.
Preliminary Amendment filed in U.S. Appl. No. 08/669,791, filed Oct. 10, 1996.
Preliminary Amendment filed in U.S. Appl. No. 10/293,941, filed Jan. 5, 2010.
Read, et al. "In vivo effects of IGF-I on gut growth and function" Elsevier Science B.V., 1994, 409-416.
Response to Office Action filed in U.S. Appl. No. 08/835,538, filed Jul. 8, 1998.
Response to Office Action filed in U.S. Appl. No. 08/835,538, filed Mar. 4, 1998.
Response to Office Action filed in U.S. Appl. No. 08/835,538, filed Dec. 7, 1999.
Response to Office Action filed in U.S. Appl. No. 10/293,941, filed Jul. 2, 2002.
Response to Office Action filed in U.S. Appl. No. 10/293,941, filed Mar. 19, 2008.
Response to Office Action filed in U.S. Appl. No. 10/293,941, filed Jan. 21, 2009.
Response to Office Action filed in U.S. Appl. No. 08/669,791, filed Dec. 10, 1997.
Response to Office Action filed in U.S. Appl. No. 08/422,540, filed Sep. 29, 1997.
Response to Office Action filed in U.S. Appl. No. 08/422,540, filed Jul. 8, 1998.
Response to Office Action filed in U.S. Appl. No. 08/422,540, filed Mar. 2, 1999.
Response to Office Action filed in U.S. Appl. No. 10/042,746, filed Aug. 15, 2005.
Response to Office Action filed in U.S. Appl. No. 08/632,533, filed Jun. 23, 1998.
Response to Office Action filed in U.S. Appl. No. 08/632,533, filed Oct. 29, 2001.
Response to Office Action filed in U.S. Appl. No. 08/632,533, filed May 28, 2002.
Response to Office Action filed in U.S. Appl. No. 12/816,312, filed Dec. 13, 2011.
Response to Restriction Requirement filed in U.S. Appl. No. 10/293,941, filed Jul. 31, 2007.
Response to Restriction Requirement filed in U.S. Appl. No. 10/293,941, filed Mar. 6, 2006.
Response to Restriction Requirement filed in U.S. Appl. No. 11/325,527, filed May 5, 2008.
Restriction Requirement issued in U.S. Appl. No. 10/293,941, dated May 1, 2006.
Restriction Requirement issued in U.S. Appl. No. 10/293,941, dated Feb. 7, 2006.
Restriction Requirement issued in U.S. Appl. No. 11/325,527 dated Nov. 5, 2007.
Restriction Requirement issued in U.S. Appl. No. 12/816,312 dated Jan. 26, 2011.
Response to Restriction Requirement in U.S. Appl. No. 12/816,312 dated Apr. 26, 2011.
Request for Continued Examination filed in U.S. Appl. No. 10/293,941, filed Oct. 26, 2009.
Request for Continued Examination filed in U.S. Appl. No. 11/325,527, filed Jul. 6, 2010.
Rothenberg, et al., "Processing of mouse proglucagon by recombinant prohormone convertase 1 and immunopurified prohormones convertase 2 in vitro", J. of Biological Chemistry, vol. 270, No. 17, 10136-10146.
Ruiz-Grande, et al., "Renal catabolism of human glucagon-like peptides 1 and 2", Can. J. Physiology Pharmacology, vol. 68, No. 12, 1990, 1568-1573.
Rudinger, Peptide Hormones, JA Parsons, Ed. 1976, 1-7.
Scott, et al., Am. J. Physiological Society, G911-G921, 1998.
Seino, et al. "Mutations in the guinea pig preproglucagon gene are restricted to a specific portion of the prohormone sequence" FEBS, 203:1 25-30 1986.
Shennen, et al., "Proglucagon expression, posttranslational processing and secretion in SV40-transformed t islet cells", Molecular and Cellular Endocrinology, vol. 67, 1989, 93-99.
Siegel, et al., "Biological activity of GLP-1 analogues with N-terminal modifications", Reg. Peptides, vol. 79, 1999, 93-102.
Sigma, "Designing custom peptides", http://www.sigma-genosys.com/peptide_design.asp (accessed Dec. 16, 2004).
Sorensen, et al., "No effect of physiological concentrations of glucagon-like peptide-2 on appetite and energy intake in normal weight subjects", Int. J. Obesity, vol. 27, 2003, 450-456.
Supplemental Response to Office Action filed in U.S. Appl. No. 08/422,540, filed Nov. 4, 1997.
Turton, et al., "A role for glucagon-like peptide-1 in the central regulation of feeding", Nature, vol. 379, 1996, 69-71.
Vertebrate, (retrieved from) http://en.wikipedia.org/wiki/Vertebrate, 2008, 2 pgs (retrieved on Sep. 19, 2008).
Voet, et al., Biochemistry, Second Edition, John Wiley & Sons, 1995, 235-241.
Watanabe, et al., "Trophic effect of glucagon-(1-21)-peptide on the isolated rat Ileal mucosal cells", Biochemical and Biophysical Research Communications, vol. 152, No. 3, 1988, 1038-1044.
Yamada, et al., "Guinea pig preprogulcagon cDNA and its gene expression in pancreas and intestine", Biomedical Research, 1988, vol. 9, No. 3, 7-11.
Cavanaugh, et al., "Isolation and structural characterization of proglucagon-derived peptides, pancreatic polypeptide, and somatostatin from the urodele amphiuma tridactylun", General and Comparative Endocrinology, 1996, vol. 101, 12-20.
Heinrich, 1984, The Journal of Biological Chemistry, 259, 14082-14087.
Lund, et al., "Anglerfish islet pre-proglucagon II" J. of Biological Chemistry 258(5) 1983 3280-3284.
Office Action issued in U.S. Appl. No. 12/976,268 dated May 22, 2012.
Office Action issued in U.S. Appl. No. 12/976,268 dated Jan. 31, 2013.
Office Action issued in U.S. Appl. No. 12/816,312 dated May 29, 2013.
Office Action issued in U.S. Appl. No. 13/794,314 dated Jun. 6, 2013.
Office Action issued in U.S. Appl. No. 13/794,314 dated Sep. 10, 2013.
Office Action issued in U.S. Appl. No. 12/976,268 dated Apr. 22, 2014.

(56) References Cited

OTHER PUBLICATIONS

Phillipe et al., "Proglucagon processing in a rat islet cell line resembles phenotype of intestine rather than pancreas" Endocrinology, vol. 119 No. 6, 1986, 2833-2839.
Response to Office Action filed in U.S. Appl. No. 12/976,268, filed Nov. 21, 2012.
Response to Office Action filed in U.S. Appl. No. 12/816,312, filed Nov. 27, 2013.
Response to Office Action filed in U.S. Appl. No. 12/976,268, filed Feb. 5, 2014.
Response to Restriction Requirement filed in U.S. Appl. No. 13/794,314, filed Jun. 28, 2013.
Restriction Requirement issued in U.S. Appl. No. 12/976,268 dated Feb. 1, 2012.
Response Restriction Requirement issued in U.S. Appl. No. 12/976,268 dated Apr. 2, 2012.

* cited by examiner

GLUCAGON-LIKE PEPTIDE-2 ANALOGS

CROSS-REFERENCE TO RELATED APPLICATIONS

This application is a divisional of U.S. patent application Ser. No. 12/816,312, filed Jun. 15, 2010, which is a divisional of U.S. patent application Ser. No. 10/293,941, filed Nov. 14, 2002, now U.S. Pat. No. 7,781,401, which is a continuation of U.S. patent application Ser. No. 09/764,070, filed Jan. 19, 2001, now abandoned, which is a divisional of U.S. patent application Ser. No. 08/835,538, filed Apr. 8, 1997, now U.S. Pat. No. 6,184,201 which is a continuation-in-part of U.S. patent application Ser. No. 08/631,273, filed Apr. 12, 1996, no abandoned, and U.S. patent application Ser. No. 08/632,533, filed Apr. 12, 1996, and a continuation-in-part of application Ser. No. 08/422,540, filed Apr. 14, 1995, now U.S. Pat. No. 5,990,077, the disclosures of which are incorporated by reference herein.

FIELD OF THE INVENTION

This invention relates to glucagon-related peptides having intestinal tissue growth promoting properties, and to their use therapeutically to treat various medical conditions resulting from the impaired growth or loss of such tissue.

BACKGROUND TO THE INVENTION

Expression of the glucagon gene yields a tissue-determined variety of peptide products that are processed from the 160 residue proglucagon product. The organization of these peptides within the proglucagon precursor was elucidated by the molecular cloning of preproglucagon cDNAs from the rat, hamster and bovine pancreas. These analyses revealed that preproglucagon contains not only the sequence of glucagon and glicentin, but also two additional glucagon-like peptides (GLP-1 and GLP-2) separated from glucagon and each other by two spacer or intervening peptides (IP-I and IP-II). These peptides are flanked by pairs of basic amino acids, characteristic of classic prohormone cleavage sites, suggesting they might be liberated after posttranslational processing of proglucagon (Drucker, Pancreas, V1990, 5(4):484).

Analysis of the peptides liberated from proglucagon in the pancreatic islets of Langerhans, for instance, suggests the primary pancreatic peptide liberated is the 29-mer glucagon, whereas glicentin, oxyntomodulin, IP-IT and the glucagon-like peptides are more prevalent in the small and large intestines. This demonstration that the glucagon-like peptides are found in the bowel has prompted research into the precise structure and putative function(s) of these newly discovered gut peptides. Most studies have focussed on GLP-1, because several lines of evidence suggested that GLP-1 may be an important new regulatory peptide. Indeed, it has been determined that GLP-1 is one of the most potent known peptidergic stimulus for insulin release, an action mediated in a glucose-dependent manner through interaction with receptors on pancreatic β cells. GLP-1 and its derivatives are in development for use in the treatment of diabetics.

The physiological roles of glicentin and oxyntomodulin, the so-called "enteroglucagons", are also under investigation, particularly with respect to regulation of acid secretion and the growth of intestinal cells. Oxyntomodulin is capable of inhibiting pentagastrin-stimulated gastric acid secretion in a dose-dependent manner. The role of glicentin in mediating the changes of intestinal adaptation and growth of the intestinal mucosa has been investigated, and the intestinotrophic effect of glicentin and its therapeutic use have recently been reported by Matsuno et al in EP 612,531 published Aug. 31, 1994.

In contrast to GLP-1 and other glucagon-related peptides, the physiological role of glucagon-like peptide GLP-2 remains poorly understood despite the isolation and sequencing of various GLP-2 homologues including human, rat, bovine, porcine, guinea pig and hamster. Using GLP-2 antisera raised against synthetic versions of GLP-2, various groups have determined that GLP-2 is present primarily in intestinal rather than pancreatic extracts (see Mojsov et al, J. Biol. Chem., 1986, 261(25):11880; Orskov et al in Endocrinology, 1986, 119(4):1467 and in Diabetologia, 1987, 30:874 and in FEBS Letters, 1989, 247(2):193; George et al, FEBS Letters, 1985, 192(2):275). With respect to its biological role, Hoosein et al report (FEBS Letters, 1984, 178(1):83) that GLP-2 neither competes with glucagon for binding to rat liver and brain tissues, nor stimulates adenylate cyclase production in liver plasma membranes, but, enigmatically, can stimulate adenylate cyclase in both rat hyopthalamic and pituitary tissue, at 30-50 pM concentrations. An elucidation of the physiological role of GLP-2 would clearly be desirable.

SUMMARY OF THE INVENTION

There have now been discovered analogs of GLP-2 which promote growth of small bowel tissue. It is accordingly a general object of the present invention to provide such GLP-2 analogs and to provide for their use therapeutically and for related purposes.

In one aspect of the invention, the GLP-2 analogs exhibit intestinotrophic activity and conform to the structural Formula 1 (SEQ ID NO: 1):

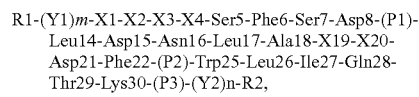

wherein

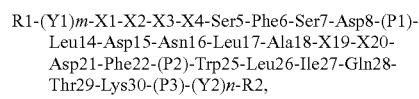

wherein
 X1 is His or Tyr
 X2 is Ala or an Ala-replacement amino acid conferring on said analog resistance to DPP-IV enzyme;
 X3 is Pro, HPro, Asp or Glu;
 X4 is Gly or Ala;
 P1 is Glu-X10-Asn-Thr-Ile or Tyr-Ser-Lys-Tyr;
 X10 is Met or an oxidatively stable Met-replacement amino acid;
 X19 is Ala or Thr;
 X20 is Arg, Lys, His or Ala;
 P2 is Ile-Asn, Ile-Ala or Val-Gln;
 P3 is a covalent bond, or is Ile, Ile-Thr or Ile-Thr-Asn;
 R1 is H or an N-terminal blocking group;
 R2 is OH or a C-terminal blocking group;
 Y1 is one or two basic amino acids selected from the group Arg, Lys, and His;
 Y2 is one or two basic amino acids selected from the group Arg, Lys, and His; and
 m and n, independently, are 0 or 1; and
wherein at least one of X1, X2, X3, X4, P1, X10, X19, X20, P2 and P3 is other than a wild type, mammalian GLP-2 residue.

Particularly preferred analogs according to Formula 1 (SEQ ID NO: 1) are those which are rendered resistant to cleavage by human DPP-IV enzyme by replacing the Ala at position X2 with an alternative amino acid. Other analogs of the invention are those which replace the oxidatively sensitive Met at position X10 with an amino acid residue which is oxidatively stable. In this manner, the analog peptides have increased stability compared to GLP-2 peptides with the wild-type Met residue at this position. Yet another preferred embodiment of the invention is the incorporation at position X20 of a basic amino acid selected from His or Lys. This substitution is advantageous when the GLP-2 analogs are chemically synthesized. The Arg residue which normally occurs at this position tends to strongly bind solvents used in peptide synthesis procedures. Substitution of the Arg allows easier formulation of the synthetically produced GLP-2 analogs into pharmaceutically acceptable compositions.

More particularly, and according to one aspect of the invention, there are provided analogs of a GLP-2 peptide selected from a mammalian GLP-2 species and N- and/or C-terminally modified forms thereof, the analogs having intestinotrophic activity and incorporating, relative to said mammalian GLP-2 peptide, at least one amino acid substitution at a position which is conserved in mammalian GLP-2's. In a preferred aspect, the GLP-2 analogs incorporate a substitution selected from:

1) incorporation at position 2 or at position 3 a replacement amino acid conferring on said analog resistance to Dipeptidyl Peptidase-IV (hereinafter referred to as DPP-IV); and
2) incorporation at position 10 of an oxidatively stable Met-replacement amino acid; and
3) incorporation at X20 of a replacement amino acid other than Arg.

In still another of its aspects, the invention provides intestinotrophic analogs of a mammalian GLP-2, preferably human. GLP-2, in which either the N- and/or C-terminus is modified by a blocking group, or additional amino acids, or the substitution of a modified or alternative amino acid. In yet another aspect, there are provided intestinotrophic analogs of mammalian GLP-2, preferably human GLP-2, in which positions X1, X5, X7, X16-X18, X25, X30, or X33 incorporate a replacement amino acid other than that found in naturally occurring mammalian GLP-2's. Optionally, in a further aspect, the invention provides intestinotrophic analogs in which from 4 to 8 residues are deleted from the C-terminus.

In another of its aspects, the invention provides a pharmaceutical composition comprising a GLP-2 analog of the present invention in a therapeutically effective amount, and preferably in an intestinotrophic amount, and a pharmaceutically acceptable carrier.

In a further aspect, the invention provides a method for promoting growth of small bowel tissue in a patient in need thereof, comprising the step of delivering to the patient an intestinotrophic amount of a GLP-2 analog of the present invention.

Besides promoting bowel growth, in another of its aspects the invention provides a method for treating a gastrointestinal disease by administering to a patient suffering from gastrointestinal disease a therapeutically effective amount of a GLP-2 analog of the invention, together with a pharmaceutically acceptable carrier, in order to reduce a pathological effect or symptom of the gastrointestinal disease.

In still another aspect of the invention, there is provided a method useful to identify intestinotrophic analogs of GLP-2, comprising the steps of 1) obtaining a GLP-2 analog conforming to Formula 1 (SEQ ID NO: 1) represented above;
2) treating a mammal with said analog using a regimen capable of eliciting an intestinotrophic effect when utilized for rat GLP-2; and
3) determining the effect of said analog on small bowel weight relative to a mock treated control mammal, whereby said intestinotrophic analog of GLP-2 is identified as an analog which elicits an increase in said weight.

DETAILED DESCRIPTION OF THE INVENTION

The invention relates to therapeutic and related uses of GLP-2 analogs, particularly for promoting growth of tissue of the small bowel. The effect on growth elicited by the present GLP-2 analogs manifests as an increase in small bowel weight, relative to a mock-treated control. In particular, GLP-2 analogs are considered to have "intestinotrophic" activity if, when assessed in the murine model exemplified herein, the analog mediates an increase in small bowel weight of at least 10% relative to a control animal receiving vehicle alone. Particularly suitable for therapeutic use are those analogs which mediate an increase of at least 20% in small bowel weight; preferred for therapeutic use are those which mediate an increase in small bowel weight of 50% or more. Intestinotrophic activity is noted most significantly in relation to the jejunum, including the distal jejunum and particularly the proximal jejunum, and is also noted in the ileum.

In addition to exhibiting intestinotrophic activity as just defined, the GLP-2 analogs of the present invention incorporate an amino acid substitution at one or more sites within a GLP-2 peptide "background", which is either a mammalian GLP-2 species per se, or is a variant of a mammalian GLP-2 species in which the C-terminus and/or the N-terminus has been altered by addition of one or two basic residues, or has been modified to incorporate a blocking group of the type used conventionally in the art of peptide chemistry to protect peptide termini from undesired biochemical attack and degradation in vivo. Thus, the present peptides incorporate an amino acid substitution in the context of any mammalian GLP-2 species, including but not limited to human GLP-2, bovine GLP-2, rat GLP-2, degu GLP-2, ox GLP-2, porcine GLP-2, guinea pig GLP-2 and hamster GLP-2, the sequences of which have been reported by many authors, including Buhl et al, J. Biol. Chem., 1988, 263(18):8621.

In one aspect of the invention, the intestinotrophic analogs of GLP-2 conform to the sequence of Formula 1 (SEQ ID NO: 1) as follows:

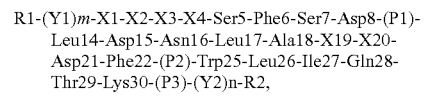

R1-(Y1)$m$-X1-X2-X3-X4-Ser5-Phe6-Ser7-Asp8-(P1)-
Leu14-Asp15-Asn16-Leu17-Ala18-X19-X20-
Asp21-Phe22-(P2)-Trp25-Leu26-Ile27-Gln28-
Thr29-Lys30-(P3)-(Y2)n-R2, wherein
X1 is His or Tyr
X2 is Ala or an Ala-replacement amino acid conferring on said analog resistance to DPP-IV enzyme;
X3 is Pro, HPro, Asp or Glu;
X4 is Gly or Ala;
P1 is Glu-X10-Asn-Thr-Ile or Tyr-Ser-Lys-Tyr;
X10 is Met or an oxidatively stable Met-replacement amino acid;
X19 is Ala or Thr;
X20 is Arg, Lys, His or Ala;
P2 is Ile-Asn, Ile-Ala or Val-Gln;
P3 is a covalent bond, or is Ile, Ile-Thr or Ile-Thr-Asn;
R1 is H or an N-terminal blocking group;

R2 is OH or a C-terminal blocking group;

Y1 is one or two basic amino acids selected from the group Arg, Lys, and His;

Y2 is one or two basic amino acids selected from the group Arg, Lys, and His; and m and n, independently, are 0 or 1; and wherein at least one of X1, X2, X3, X4, P1, X10, X19, X20, P2 and P3 is other than a wild type, mammalian GLP-2 residue.

Wild-type mammalian GLP-2 residues which occur at a specific position are determined by aligning the sequences of GLP-2's isolated from different mammalian species and comparing the sequence to the human sequence (SEQ ID NO: 2), reproduced below, for convenience:

```
His-Ala-Asp-Gly-Ser-Phe-Ser-Asp-Glu-Met-Asn-
1               5                   10

Thr-Ile-Leu-Asp-Asn-Leu-Ala-Ala-Arg-Asp-Phe-
         15                  20

Ile-Asn-Trp-Leu-Ile-Gln-Thr-Lys-Ile-Thr-Asp
         25                  30
```

The amino acid residues which, for purposes of this application, are known to occur at specific positions in wild type mammalian GLP-2's are the following: position X13 may be Ile or Val; position X16 may be Asn or Ser; position X19 may be Alanine or Threonine; position X20 may be Arg or Lys; position X27 may be Ile or Leu; and position X28 may be Gln or His.

The present GLP-2 analogs may incorporate desired amino acid substitutions into a "background" which is an N-terminally or C-terminally modified form of a mammalian GLP-2 peptide. Such analogs are represented in Formula 1 (SEQ ID NO: 1) as those in which R1 constitutes an N-terminal blocking group, and/or when m is 1 then Y1 is one or two basic amino acids such as Arg or Lys; and/or R2 is a C-terminal blocking group; and/or when n is 1 then Y2 is independently, one or two basic amino acids such as Arg or Lys.

In preferred embodiments of the invention, the GLP-2 analog is an analog of full length GLP-2, i.e., GLP-2 (1-33), and P3 is accordingly the sequence Ile-Thr-Asn. Alternatively, the GLP-2 analogs may be C-terminally truncated, to yield GLP-2 (1-32) forms in which P3 is Ile-Thr, or GLP-2 (1-31) forms in which P3 is Ile, or GLP-2 (1-30) forms in which P3 is a covalent bond.

The "blocking groups" represented by R1 and R2 are chemical groups that are routinely used in the art of peptide chemistry to confer biochemical stability and resistance to digestion by exopeptidase. Suitable N-terminal protecting groups include, for example, $C_{1-5}$ alkanoyl groups such as acetyl. Also suitable as N-terminal protecting groups are amino acid analogues lacking the amino function, for example, desamino-Tyr1. Suitable C-terminal protecting groups include groups which form ketones or amides at the carbon atom of the C-terminal carboxyl, or groups which form esters at the oxygen atom of the carboxyl. Ketone and ester-forming groups include alkyl groups, particularly branched or unbranched $C_{1-5}$ alkyl groups, e.g., methyl, ethyl and propyl groups, while amide-forming groups include amino functions such as primary amine, or alkylamino functions, e.g., mono-$C_{1-5}$ alkylamino and di-$C_{1-5}$ alkylamino groups such as methylamino, ethylamino, dimethylamino, diethylamino, methylethylamino and the like. Amino acid analogues are also suitable for protecting the C-terminal end of the present compounds, for example, decarboxylated amino acid analogues such as agmatine.

Embodiments of the invention specifically include such analogs in which m is 0 and R1 is a blocking group such as acetyl; and analogs in which m is 0 and R2 is a C-terminal blocking group such as an amide or an amine, e.g., —NH2.

In a preferred aspect of the invention, the GLP-2 analogs are analogs of either human GLP-2 or of rat GLP-2. Human GLP-2 is herein referred to interchangably as hGLP-2 (1-33). Rat GLP-2 has the amino acid sequence of human GLP-2, but incorporates at position 19 a Thr residue instead of an Ala residue. Rat GLP-2 is accordingly referenced herein either as rGLP-2 (1-33) or as the $Thr^{19}$ analog of human GLP-2, i.e., as $[Thr^{19}]$hGLP-2 (1-33).

In particularly preferred embodiments of the invention, with respect to both the Formula 1 (SEQ ID NO: 1) analogs and the more specific human or rat GLP-2 analogs, the GLP-2 analogs incorporate an amino acid substitution selected from:

1) incorporation at X2 and/or at X3 of a replacement amino acid which renders said analog resistant to cleavage by DPP-IV enzyme;

2) incorporation at X10 of an oxidatively stable Met-replacement amino acid; and 3) incorporation at X20 of a replacement amino acid other than Arg.

In still another of its aspects, the invention provides intestinotrophic analogs of a mammalian GLP-2, preferably human GLP-2, in which either the N- and/or C-terminus is modified by a blocking group, or additional amino acids, or the substitution of a modified or alternative amino acid. In yet another aspect, there are provided intestinotrophic analogs of mammalian GLP-2, preferably human GLP-2, in which positions X1, X5, X7, X16-X18, X25, X30, or X33 incorporate a replacement amino acid other than that found in naturally occurring mammalian GLP-2's. Optionally, in a further aspect, the invention provides intestinotrophic analogs in which from 4 to 8 residues are deleted from the C-terminus.

The DPP-IV-resistant class of GLP-2 analogs possess particularly advantageous properties. As is demonstrated herein, mammalian GLP-2 species have been found to be sensitive to cleavage by DPP-IV enzyme. It has also been found that this sensitivity to DPP-IV is the result of the recognition sequence $Ala^2 Asp^3$ found in all mammalian forms of GLP-2. There are accordingly provided by the present invention a class of GLP-2 analogs which incorporate at X2 and/or X3 a replacement amino acid which confers on the GLP-2 analog relative resistance to DPP-IV mediated cleavage, as determined by any convenient in vitro or in vivo assessment technique that is able to detect the presence of GLP-2 digestion products. A DPP-IV resistant GLP-2 analog is revealed as that GLP-2 analog which is processed or degraded at a rate that is measurably slower than the rate at which human GLP-2 is processed or degraded, under the same conditions.

An assay suitable for assessing DPP-IV sensitivity and resistance is described below in Example 3, in the context of results actually obtained.

The X2 class of GLP-2 analogs is preferred herein. These $Ala^2$-substituted GLP-2 analogs can incorporate at X2 a structurally wide variety of Ala-replacement amino acids to achieve relative resistance to DPP-IV digestion. A similarly wide variety of Ala-replacement amino acids allow also for the retention by the analog of intestinotrophic activity. For purposes of identifying those DPP-IV-resistant X2 analogs that also retain intestinotrophic activity, the X2 analogs showing DPP-TV resistance are screened in the assay of intestinotrophic activity described below in Example 4.

In embodiments of the present invention, the $Ala^2$ replacements include stereoisomers of amino acids that would otherwise be substrates for DPP-IV, for example D-Ala, D-HPr, βAla, t-butyl-Gly, L-penicillamin, α-aminobutyric acid, aminoisobutyric acid, norvaline, L-phenyl-Gly, and D-Pro, and naturally occurring amino acids, for example, Glu, Lys, Ile, Ser, Asp, Phe, Lys, Met, Asn, Pro, Gln, Thr, Tyr, Gly and Val. In specific embodiments of the invention, there are provided the following Ala$^2$-substituted GLP-2 analogs: [D-Ala$^2$] rGLP-2 (1-33), [Gly$^2$]rGLP-2 (1-33), [Val$^2$]rGLP-2 (1-33) [Gly$^2$]hGLP-2 (1-33), [tBuGly$^2$]hGLP-2, [Asp$^2$]hGLP-2 (1-33), [Glu$^2$]hGLP-2 (1-33), [Phe$^2$]hGLP-2 (1-33) [His$^2$] hGLP-2 (1-33), [Ile$^2$]hGLP-2 (1-33), [Lys$^2$]hGLP-2 (1-33) [Met$^2$]hGLP-2 (1-33), [Asn$^2$]hGLP-2 (1-33) [Pro$^2$]hGLP-2 (1-33) [Gln$^2$]hGLP-2 (1-33), [Ser$^2$]hGLP-2 (1-33), [Thr$^2$] hGLP-2 (1-33), [Val$^2$]hGLP-2 (1-33), [Tyr$^2$]hGLP-2 (1-33), [D-Ala$^2$]hGLP-2 (1-33), [Pen$^2$]hGLP-2 (1-33), [bAla$^2$] hGLP-2 (1-33), [aAbu$^2$]hGLP-2 (1-33), [Nval$^2$]hGLP-2 (1.33), [PhGly$^2$]hGLP-2 (1-33), and [Aib$^2$]hGLP-2 (1-33).

The X2 GLP-2 analogs may incorporate amino acid replacements at other positions. In embodiments of the invention, such analogs include those carrying amino acid substitutions also at one or more of positions X1, X3, X4, X10, X19, X20 and X24, and therefore include those which, according to Formula 1 (SEQ ID NO: 1), include at least one of the following substitutions: X1 is Tyr; X3 is Glu; X4 is Ala; P1 is Glu-X10-Asn-Thr-Ile where X10 is other than Met or P1 is Tyr-Ser-Lys-Tyr; X10 is an oxidatively stable Met-replacement amino acid; X19 is Thr; X20 is Lys or Ala; P2 is Val-Gln and P3 is a covalent bond, Ile, or Ile-Thr or Ile-Thr-Asn.

In embodiments of the present invention, the X2 analogs of GLP-2 include those which also incorporate one of the following substitutions: X1 is Ala; X3 is Ala; X4 is Ala; X10 is an oxidatively stable Met-replacement amino acid such as Val, Ile, Asn, Glx, Tyr, Phe, and preferably Leu, Nle, Ala, Ser, and Gly; and P2 is Ile-Ala. In specific embodiments of the invention, there are provided the following GLP-2 analogs: [D-Ala$^2$Thr$^{19}$]hGLP-2 (1-33); [Gly$^2$Thr$^{19}$]hGLP-2 (1-33); [Val$^2$Thr$^{19}$]hGLP-2 (1-33); [Gly$^2$Ala$^{24}$]hGLP-2 (1-33); [Gly$^2$Ala$^{10}$]hGLP-2 (1-33); [Ala$^1$Gly$^2$]hGLP-2 (1-33); [Gly$^2$Ala$^3$]hGLP-2 (1-33) and [Gly$^2$Ala$^4$]hGLP-2 (1-33).

In a related embodiment, the X2 analogs include those which include the following substitutions: GLP-2[Gly$^2$Ala$^8$] hGLP-2; [Gly$^2$Ala$^{11}$]hGLP-2; [Gly$^2$Ala$^{21}$]hGLP-2; [Gly$^2$Ala$^9$]hGLP-2; [Gly$^2$Ala$^{16}$]hGLP-2; [Gly$^2$Ala$^{17}$]hGLP-2; [Gly$^2$Ala$^{28}$]hGLP-2; [Gly$^2$Ala$^5$]hGLP-2; [Gly$^2$Ala$^{31}$] hGLP-2; [Gly$^2$Ala$^{27}$]hGLP-2; [Gly$^2$Ala$^{12}$]hGLP-2; [Gly$^2$Ala$^{13}$]hGLP-2; [Gly$^2$Ala$^7$]hGLP-2; [Gly$^2$Ala$^6$]hGLP-2; [Ser$^2$, Gln$^3$]hGLP-2 (1-33); [Gly$^2$, Ala$^{25}$]hGLP-2 (1-33); [Gly$^2$, Ala$^{26}$]hGLP-2 (1-33); [Gly$^2$, Ala$^{/4}$]hGLP-2 (1-33); [Gly$^2$, Ala$^{23}$]hGLP-2 (1-33); [Gly$^2$, Ala$^{30}$]hGLP-2 (1-33); [Tyr$^1$, Gly$^2$]hGLP-2 (1-33); [Gly$^2$, Arg$^{34}$]hGLP-2 (1-34); and [Gly$^2$, Tyr$^{34}$]hGLP-2 (1-34).

Alternatively, in the case where X2 is Ala, hPr or Pro, DPP-IV resistance can be conferred by replacing Asp$^3$ with an Asp-replacement amino acid, X3 which is Pro or hPr.

The present invention also provides, as another class of GLP-2 analogs, those analogs in which X10 represents an oxidatively stable, Met-replacement amino acid. It has been found that the intestinotrophic activity of mammalian GLP-2 is reduced when the Met in position 10 is oxidized, and also that intestinotrophic activity is retained when replacement amino acids insensitive to oxidation are substituted for Met$^{10}$ replacement. Such Met$^{10}$-substituted GLP-2 analogs are accordingly more stable during synthesis, work-up and storage. In embodiments of the present invention, such X10 analogs of GLP-2 are analogs of human GLP-2. In a specific embodiments of the invention, such analogs include: [Ser$^{10}$] hGLP-2 (1-33); [Nle$^{10}$]hGLP-2 (1-33); [Ala$^{10}$]hGLP-2 (1-33); [Leu$^{10}$]rGLP-2 (1-33); [Met(O)]ratGLP-2 (1-33); and [Nle$^{10}$]ratGLP-2 (1-33).

The X10 analogs may also incorporate amino acid substitutions at one or more positions other than X10. As noted above, such analogs include, for instance, those incorporating substitutions at X2, and those in which P1 is Tyr-Ser-Lys-Tyr, as well as those in which any one of the X substituents or the P substituents represented in Formula 1 (SEQ ID NO: 1) are other than wild type residues or sequences. In specific embodiments, the GLP-2 analogs include [Gly$^2$Ala$^{10}$] hGLP-2 (1-33) and [Tyr$^9$Ser$^{10}$Lys$^{11}$Tyr$^{12}$desIle$^{13}$]hGLP-2 (1-33).

In other embodiments of the invention, the GLP-2 analogs incorporate single amino acid substitutions in the context of the mammalian GLP-2 peptide background in which they are introduced. Such analogs include, for example, those mammalian GLP-2 analogs and particularly the human GLP-2 analogs in which X1 is Tyr; X3 is Glu; X4 is Ala; P1 is Tyr-Ser-Lys-Tyr-(desIle); P2 is Ile-Ala or Val-Gln; and P3 is a covalent bond, or is Ile or Ile-Thr.

Still other GLP-2 analogs of the invention incorporate alterations of the N- or C-terminus by the addition of amino acids, by blocking groups, or by substituted amino acids. There are also provided intestinotrophic analogs of mammalian GLP-2, preferably human GLP-2, in which positions X1, X5, X7, X16-X18, X25, X30, or X33 incorporate a replacement amino acid other than that found in naturally occurring mammalian GLP-2's. Optionally, the invention provides intestinotrophic analogs in which from 4 to 8 residues are deleted from the C-terminus. Specific embodiments of such intestinotrophic analogs include: Ac-ratGLP-2 (1-33); ratGLP-2 (1-30); ratGLP-2 (1-25); ratGLP-2 (1-33)amide; [Arg-$^2$, Arg-$^1$]ratGLP-2 (2-33) [Pro$^1$]hGLP-2 (1-33); [Gln$^{20}$] hGLP-2 (1-33); [Asp$^1$]hGLP-2 (1-33); [Tyr$^{34}$]hGLP-2 (1-34); [desNH2Tyr$^1$]hGLP-2 (1-33); [Thr$^5$]hGLP-2 (1-33); [Ser$^{16}$, Arg$^{17}$, Arg$^{18}$]hGLP-2 (1-33); [Agm$^{34}$]hGLP-2 (1-34); [Arg$^{30}$]hGLP-2 (1-33); [Ala$^5$, Ala$^7$]hGLP-2 (1-33); [Glu$^{33}$] hGLP-2 (1-33); [Phe$^{25}$]hGLP-2 (1-33); and [Tyr$^{25}$]hGLP-2 (1-33).

The present GLP-2 analogs can be synthesized using standard techniques of peptide chemistry and can be assessed for intestinotrophic activity, all according to the guidance provided herein. With respect to synthesis, the selected GLP-2 analog can be prepared by a variety of techniques well known for generating peptide products. Those GLP-2 analogs that incorporate only L-amino acids can be produced in commercial quantities by application of recombinant DNA technology. For this purpose, DNA coding for the desired. GLP-2 analog is incorporated into an expression vector and transformed into a microbial, e.g., yeast, or other cellular host, which is then cultured under conditions appropriate for GLP-2 expression. A variety of gene expression systems have been adapted for this purpose, and typically drive expression of the desired gene from expression regulatory elements used naturally by the chosen host. Because GLP-2 does not require post translational glycosylation for its activity, its production may most conveniently be achieved in bacterial hosts such as E. coli. For such production, DNA coding for the selected GLP-2 peptide may usefully be placed under expression controls of the lac, trp or PL genes of E. coli. As an alternative to expression of DNA coding for the GLP-2 per se, the host can be adapted to express GLP-2 peptide as a fusion protein in which the GLP-2 is linked releasably to a carrier protein that facilitates isolation and stability of the expression product.

In an approach universally applicable to the production of a selected GLP-2 analog, and one used necessarily to produce GLP-2 analogs that incorporate non-genetically encoded amino acids and N- and C-terminally derivatized forms, the well established techniques of automated peptide synthesis are employed, general descriptions of which appear, for example, in J. M. Stewart and J. D. Young, Solid Phase Peptide Synthesis, 2nd Edition, 1984, Pierce Chemical Company, Rockford, Ill.; and in M. Bodanszky and A. Bodanszky, The Practice of Peptide Synthesis, 1984, Springer-Verlag, New York; Applied Biosystems 430A Users Manual, 1987, ABI Inc., Foster City, Calif. In these techniques, GLP-2 analog is grown from its C-terminal, resin-conjugated residue by the sequential addition of appropriately protected amino acids, using either the Fmoc or tBoc protocols, as described for instance by Orskov et al, 1989, supra.

For the incorporation of N— and/or C— blocking groups, protocols conventional to solid phase peptide synthesis methods can also be applied. For incorporation of C-terminal blocking groups, for example, synthesis of the desired peptide is typically performed using, as solid phase, a supporting resin that has been chemically modified so that cleavage from the resin results in a GLP-2 peptide having the desired C-terminal blocking group. To provide peptides in which the C-terminus bears a primary amino blocking group, for instance, synthesis is performed using a p-methylbenzhydrylamine (MBHA) resin so that, when peptide synthesis is completed, treatment with hydrofluoric acid releases the desired C-terminally amidated peptide. Similarly, incorporation of an N-methylamine blocking group at the C-terminus is achieved using N-methylaminoethyl-derivatized DVB resin, which upon HF treatment releases peptide bearing an N-methylamidated C-terminus. Protection of the C-terminus by esterification can also be achieved using conventional procedures. This entails use of resin/blocking group combination that permits release of side-chain protected peptide from the resin, to allow for subsequent reaction with the desired alcohol, to form the ester function. FMOC protecting groups, in combination with DVB resin derivatized with methoxyalkoxybenzyl alcohol or equivalent linker, can be used for this purpose, with cleavage from the support being effected by TFA in dichloromethane. Esterification of the suitably activated carboxyl function, e.g., with DCC, can then proceed by addition of the desired alcohol, followed by deprotection and isolation of the esterified GLP-2 peptide.

Incorporation of N-terminal blocking groups can be achieved while the synthesized GLP-2 peptide is still attached to the resin, for instance by treatment with suitable anhydride and nitrile. To incorporate an acetyl blocking group at the N-terminus, for instance, the resin-coupled peptide can be treated with 20% acetic anhydride in acetonitrile. The N-blocked GLP-2 analog can then be cleaved from the resin, deprotected and subsequently isolated.

Once the desired GLP-2 analog has been synthesized, cleaved from the resin and fully deprotected, the peptide is then purified to ensure the recovery of a single oligopeptide having the selected amino acid sequence. Purification can be achieved using any of the standard approaches, which include reversed-phase high-pressure liquid chromatography (RP-HPLC) on alkylated silica columns, e.g., $C_4$-, $C_8$-, or $C_{18}$-silica. such column fractionation is generally accomplished by running linear gradients, e.g., 10-90%, of increasing % organic solvent, e.g., acetonitrile, in aqueous buffer, usually containing a small amount (e.g., 0.1%) of pairing agent such as TFA or TEA. Alternatively, ion-exchange HPLC can be employed to separate peptide species on the basis of their charge characteristics. Column fractions are collected, and those containing peptide of the desired/required purity are optionally pooled. In one embodiment of the invention, the GLP-2 analog is then treated in the established manner to exchange the cleavage acid (e.g., TFA) with a pharmaceutically acceptable acid, such as acetic, hydrochloric, phosphoric, maleic, tartaric, succinic and the like, to generate a pharmaceutically acceptable acid addition salt of the peptide.

For administration to patients, the GLP-2 analog or its salt is desirably provided in pharmaceutically acceptable form, e.g., as a preparation that is sterile-filtered, e.g., through a 0.22μ filter, and substantially pyrogen-free. Desirably, the GLP-2 analog to be formulated migrates as a single or individualized peak on HPLC, exhibits uniform and authentic amino acid composition and sequence upon analysis thereof, and otherwise meets standards set by the various national authorities which regulate quality of pharmaceutical products.

For therapeutic use, the chosen GLP-2 analog is formulated with a carrier that is pharmaceutically acceptable and is appropriate for delivering the peptide by the chosen route of administration. Suitable pharmaceutically acceptable carriers are those used conventionally with peptide-based drugs, such as diluents, excipients and the like. Reference may be made to "Remington's Pharmaceutical Sciences", 17th Ed., Mack Publishing Company, Easton, Pa., 1985, for guidance on drug formulations generally. In one embodiment of the invention, the compounds are formulated for administration by infusion, e.g., when used as liquid nutritional supplements for patients on total parenteral nutrition therapy, or by injection, e.g., sub-cutaneously, intramuscularly or intravenously, and are accordingly utilized as aqueous solutions in sterile and pyrogen-free form and optionally buffered to physiologically tolerable pH, e.g., a slightly acidic or physiological pH. Thus, the compounds may be administered in a vehicle such as distilled water or, more desirably, in saline, phosphate buffered saline or 5% dextrose solution. Water solubility of the GLP-2 analog may be enhanced, if desired, by incorporating a solubility enhancer, such as acetic acid.

The aqueous carrier or vehicle can be supplemented for use as injectables with an amount of gelatin that serves to depot the GLP-2 analog at or near the site of injection, for its slow release to the desired site of action. Concentrations of gelatin effective to achieve the depot effect are expected to lie in the range from 10-20%. Alternative gelling agents, such as hyaluronic acid, may also be useful as deputing agents.

The GLP-2 analogs of the invention may also be formulated as a slow release implantation device for extended and sustained administration of GLP-2 analog. Examples of such sustained release formulations include composites of biocompatible polymers, such as poly lactic acid), polylactic-co-glycolic acid), methylcellulose, hyaluronic acid, collagen, and the like. The structure, selection and use of degradable polymers in drug delivery vehicles have been reviewed in several publications, including, A. Domb et al., *Polymers for Advanced Technologies* 3:279-292 (1992). Additional guidance in selecting and using polymers in pharmaceutical formulations can be found in the text by M. Chasin and R. Langer (eds.), "Biodegradable Polymers as Drug Delivery Systems," Vol. 45 of "Drugs and the Pharmaceutical. Sciences," M. Dekker, New York, 1990. Liposomes may also be used to provide for the sustained release of a GLP-2 analog. Details concerning how to use and make liposomal formulations of drugs of interest can be found in, among other places, U.S. Pat. No. 4,944,948; U.S. Pat. No. 5,008,050; U.S. Pat. No. 4,921,706; U.S. Pat. No. 4,927,637; U.S. Pat. No. 4,452,747; U.S. Pat. No. 4,016,100; U.S. Pat. No. 4,311,712; U.S. Pat. No. 4,370,349; U.S. Pat. No. 4,372,949; U.S. Pat. No. 4,529,561; U.S. Pat. No. 5,009,956; U.S. Pat. No. 4,725,442; U.S. Pat. No. 4,737,323; U.S. Pat. No. 4,920,016. Sustained release formulations are of particular interest when it is desirable to provide a high local concentration of a GLP-2 analog.

The GLP-2 analog can be utilized in the form of a sterile-filled vial or ampoule, that contains an intestinotrophic amount of the peptide, in either unit dose or multi-dose amounts. The vial or ampoule may contain the GLP-2 analog and the desired carrier, as an administration-ready formulation. Alternatively, the vial or ampoule may contain the GLP-2 peptide in a form, such as a lyophilized form, suitable for reconstitution in a suitable carrier, such as phosphate-buffered saline.

As an alternative to injectable formulations, the GLP-2 analog may be formulated for administration by other routes. Oral dosage forms, such as tablets, capsules and the like, can be formulated in accordance with standard pharmaceutical practice. According to the present invention, the GLP-2 analog is administered to treat patients that would benefit from growth of small bowel tissue. The effects of GLP-2 analog on this tissue, as evidenced by the results exemplified herein, is dramatic and would clearly benefit those patients suffering from diseases or conditions marked by abnormalities in the small intestinal tract mucosa, which include ulcers and inflammatory disorders; congenital or acquired digestion and absorption disorders including malabsorption syndromes; and diseases and conditions caused by loss of small bowel mucosal function particularly in patients undergoing extended parenteral feeding or who, as a result of surgery, have undergone resection of the small bowel and suffer from short-gut syndrome and cul-de-sac syndrome. Therapeutic treatment with GLP-2 analog is administered so as to reduce or eliminate the disease symptoms and/or improve the nutritional status in these patients associated with their reduced intestinal tract mucosal function. For example, GLP-2 analog is administrated to a patient with an inflammatory bowel condition in an amount sufficient to ameliorate the intestinal discomfort and diarrhea caused by the condition. Additionally, GLP-2 analog may be administered to patients with malabsorption disorders so as to enhance the nutritional absorption and thereby improve the nutritional status of such patients.

In general, patients who would benefit from increased small intestinal mass and consequent increased small bowel mucosal function are candidates for treatment with GLP-2 analog. Particular conditions that may be treated with GLP-2 analog include the various forms of sprue including celiac sprue which results from a toxic reaction to α-gliadin from wheat, and is marked by a tremendous loss of villae of the small bowel; tropical sprue which results from infection and is marked by partial flattening of the villae; hypogammaglobulinemic sprue which is observed commonly in patients with common variable immunodeficiency or hypogammaglobulinemia and is marked by significant decrease in villus height. The therapeutic efficacy of the GLP-2 analog treatment may be monitored by enteric biopsy to examine the villus morphology, by biochemical assessment of nutrient absorption, by patient weight gain, or by amelioration of the symptoms associated with these conditions. Other conditions that may be treated with GLP-2 analog, or for which GLP-2 analog may be useful prophylactically, include radiation enteritis, infectious or post-infectious enteritis, regional enteritis (Crohn's disease), small intestinal damage due to toxic or other chemotherapeutic agents, and patients with short bowel syndrome.

The therapeutic dosing and regimen most appropriate for patient treatment will of course vary with the disease or condition to be treated, and according to the patient's weight and other parameters. The results presented hereinbelow demonstrate that a dose of GLP-2 peptide equivalent to about 100 μg/kg (or less) administered twice daily over 10 days can generate very significant increases in small bowel mass. It is expected that much smaller doses, e.g., in the μg/kg range, and shorter or longer duration or frequency of treatment, will also produce therapeutically useful results, i.e., a statistically significant increase particularly in small bowel mass. Also, it is anticipated that the therapeutic regimen will include the administration of maintenance doses appropriate for reversing tissue regression that occurs following cessation of initial treatment. The dosage sizes and dosing regimen most appropriate for human use are guided by the results herein presented, and can be confirmed in properly designed clinical trials.

An effective dosage and treatment protocol may be determined by conventional means, starting with a low dose in laboratory animals and then increasing the dosage while monitoring the effects, and systematically varying the dosage regimen as well. Numerous factors may be taken into consideration by a clinician when determining an optimal dosage for a given subject. Primary among these is the amount of GLP-2 normally circulating in the plasma, which is on the order of 151 pmol/ml in the resting state, rising to 225 pmol/ml after nutrient ingestion for healthy adult humans. Orskow, C. and Heist, J. J., 1987, Scand. J. Clin. Lav. Invest. 47:165. Additional factors include the size of the patient, the age of the patient, the general condition of the patient, the particular disease being treated, the severity of the disease, the presence of other drugs in the patient, the in vivo activity of the GLP-2 analog and the like. The trial dosages would be chosen after consideration of the results of animal studies and the clinical literature. It will be appreciated by the person of ordinary skill in the art that information such as binding constants and Ki derived from in vitro GLP-2 binding competition assays may also be used in calculating dosages, as well as the calculated half-life of the GLP-2 analog in vivo.

A typical human dose of a GLP-2 peptide would be from about 10 μg/kg body weight/day to about 10 mg/kg/day, preferably from about 50 μg/kg/day to about 5 mg/kg/day, and most preferably about 100 μg/kg/day to 1 mg/kg/day. As the GLP-2 analogs of the invention can be up to 10 to even 100 times more potent than GLP-2, a typical dose of such a GLP-2 analog may be lower, for example, from about 100 ng/kg body weight/day to 1 mg/kg/day, preferably 1 μg/kg/day to 500 μg/kg/day, and even more preferably 1 μg/kg/day to 100 μg/kg/day.

Similarly, the intestinotrophic GLP-2 analogs of the invention are also useful for both augmenting bowel growth and treating inflammatory disorders in livestock and pets.

Example 1

GLP-2 Analog Synthesis

Solid phase peptide synthesis (SPPs) is carried out manually in a 300 milliliter (ml) vessel on a 3 millimole (mmole) scale using 6 grams (g) of chloromethyl (Merrifield) resin (for C-terminal free acid peptides) with a substitution of 0.5 milliequivalents (meq) per gram. Amino acids are protected at the amino-terminus with the t-butyloxycarbonyl (tBoc) group. The side-chains of trifunctional amino acids are protected with the benzyl (Bz, for serine and threonine), benzyloxymethyl (BOM, for histidine), 2-bromobenzyloxycarbonyl (2-BrZ, for tyrosine), 2-chlorobenzyloxycarbonyl (2-ClZ, for lysine), cyclohexyl (cHex, for aspartic and glutamic acids), and tosyl (Tos, for arginine) groups. The first amino acid is coupled to the chloromethyl resin through esterification of the protected amino acid in the presence of potassium fluoride (KF). C-terminal amide peptides are synthesized on a 4-methylbenzhydrylamine (MBHA) resin on a 3 mmol scale using 6 g of resin with a substitution of 0.5 meq/g. The first amino acid is coupled to the MBHA resin according to the procedure described for peptide elongation.

Amino-group deprotection is carried out using 50% trifluoroacetic acid (TFA) in dichloromethane ($CH_2Cl_2$), followed by neutralization using two washes of 10% triethylamine ($Et_3N$) in $CH_2Cl_2$. Peptide elongation is carried out using N,N-dicyclohexylcarbodiimide/1-hydroxybenzotriazole (DCC/HOBt) activation in $CH_2Cl_2$/dimethylformamide (DMF). The growing peptide chain is capped after each elongation step with 20% $Ac_2O$ in $CH_2Cl_2$. The peptide-resin is washed after each elongation, capping and deprotection step with isopropanol (iPrOH) and methanol (MeOH). The washes are repeated once. N-terminal acetyl peptides are prepared by acetylation of the terminal amino-group with 20% $Ac_2O$ in $CH_2Cl_2$ after deprotection and neutralization as described. Resin-bound products are routinely cleaved by a low-high procedure using hydrogen fluoride (HF) containing dimethylsulfide (DMS) and p-cresol as scavengers.

Crude peptides are purified by preparative high pressure liquid chromatography (HPLC) using a Vydac C18, 15-20 in wide-pore, 2 inch×12 inch, reverse-phase silica column using gradient elution with 0.1% TFA in water modified with acetonitrile. Elution is monitored at 220 nanometers (nm). Each fraction collected is analyzed for purity by analytical HPLC using a Vydac C18, 5 μm, 4.6×254 millimeter (mm), reverse-phase silica column by gradient elution using 0.1% TFA in water modified with acetonitrile, and monitored at 215 nm. Fractions demonstrating greater than 95% purity are combined and lyophilized. Acetate salts of the peptides are prepared from the TFA salts by dissolution of the lyophilized powder in water, with addition of acetonitrile to aid in dissolution where necessary. The solution is passed through a protonated Bio-Rex-70 cation exchange resin. The resin is washed with 5 bed-volumes of water, and the resin-bound peptide is eluted with 50% acetic acid in water. The eluent is diluted with water and lyophilized.

The final lyophilized powder is analyzed for purity by two analytical reverse-phase HPLC methods using a Vydac C18, 5 μm, 4.6×254 mm reverse-phase silica column. The two solvent systems used are a gradient of water adjusted to pH 2.25 with triethylamine phosphate, modified with acetonitrile, and a gradient of 0.1% TFA in water, modified with acetonitrile. The column eluent is monitored at 215 nm. The identity of each product is confirmed by amino acid analysis and by electrocopy-mass spectroscopy.

The GLP-2 analogs are next formulated as described below in Example 2. Each of the GLP-2 analogs is fully soluble in water at room temperature unless otherwise noted.

Example 2

GLP-2 Analog Formulation

The GLP-2 analogs were formulated for injection either in phosphate buffered saline or as a gelatin-containing depot formulation. For the PBS-formulated GLP-2 analog preparations, a 10× stock PBS solution was first prepared, using 80 g NaCl (BDH ACS 763), 2 g KCl (BDH ACS 645), 11.5 g $Na_2HPO_4$ (Anachemia AC-8460), and 2 g $KH_2PO_4$ (Malinckrodt AR7100), which was brought to a total volume of one liter with sterile distilled water. The final working solution was obtained by 10:1 dilution of the stock solution with sterile distilled water and adjusted to pH 7.3-7.4 if necessary, using sufficient volumes of 10N NaOH. The working solution was then autoclaved for 30 minutes. In the final working PBS solution, concentrations were 137 mM NaCl, 2.7 mM KCl, 4.3 mM $Na_2HPO_4.7H_2O$, and 1.4 mM $KH_2PO_4$.

The GLP-2 analog, as a powdered peptide, is added to the working PBS solution as required to generate formulations having the desired peptide concentrations. For example, to generate a PBS solution of GLP-2 analog at 130 mg/l, 5.2 mg of GLP-2 analog is dissolved in 40 ml of PBS to yield a GLP-2 concentration of 130 μg/ml, 0.5 ml is injected twice daily.

To generate the gelatin-based GLP-2 analog formulations, a gelatin solution was first prepared by dissolving 12 grams of gelatin (Sigma, G-8150 Lot #54HO7241 Type A from Porcine skin [9000-70-8]~300 Bloom) in 100 ml distilled water. The gelatin solution was then autoclaved, warmed at 37° C., and the GLP-2 peptide previously dissolved in phosphate buffered saline as described above was then added to achieve specific, desired peptide concentrations. For instance, to generate a gelatin-based PBS solution of the GLP-2 at a concentration of 130 mg/, 10 ml of a PBS solution prepared with 5.2 mg of GLP-2 was diluted with 30 ml of the 20% working gelatin solution as first described above. The solution was mixed by gentle pipeting, to yield a final solution of 130 mg/l GLP-2 in PBS/15% gelatin.

Example 3

Assay for Resistance to Dipeptidyl Peptidase IV

The following peptides were tested for resistance to dipeptidyl peptidase IV (DPP-IV): a control peptide, rGLP-2; the [D-Ala$^2$]rGLP-2 analog; and the [Gly$^2$]rGLP-2 analog. To perform the assay, 2.5 microliters (μl) of a solution of human placental DPP-IV (Calbiochem, La Jolla, Calif., cat. #317624) containing 0.125 milliunits (mU) of enzyme in 50% glycerol, 10 mM Tris, pH 7.8, EDTA and 0.02% $NaN_3$ was added to 50 μl of a solution of the test peptide prepared at a concentration of 0.2 mg/ml in PBS at pH 7.4. The mixture was incubated at 37° C. in a circulating water bath for 24 hours. The incubation was quenched by the addition of 50 μl of a solution of diprotin A prepared at a concentration of 4 mg/ml in PBS. Each peptide was tested in duplicate.

Each sample was analyzed by reverse-phase (RP) HPLC as follows: 90 μl of the quenched incubation mixture was injected onto a Rainin Dynamax 300 Å, C18, 5 micron, 4.6× 250 millimeter column. The samples were eluted with 0.1% trifluoroacetic acid (TFA) in water modified with 0.1% acetonitrile using a linear gradient and a flow rate of 1 ml per minute. Sample components were detected at 214 nanometers (nm). The extent of cleavage was measured by relative integration of the peak corresponding to the cleavage product compared to that of the remaining undigested parent peptide. The cleavage product of the control peptide, rGLP-2 (1-33), which should be rGLP-2 (3-33), was confirmed to have result from cleavage between residues Ala$^2$ and Asp$^3$ by comparison of the retention time of this component to that of a synthetic peptide standard, rGLP-2 (3-33), and by collection of the product from the HPLC and analysis by mass spectrometry.

After the 24 hour incubation, 22% of the control peptide, rGLP-2, was cleaved by DPP-IV. No cleavage products were detected for the peptides [D-Ala$^2$]rGLP-2 and [Gly$^2$]rGLP-2 after 24 hours.

Example 4

GLP-2 Analog Assessment

Recipients were. CD1 mice obtained from Charles River Laboratory (Ontario, Canada). The CD1 mice were agedmatched females at time of injection (n=3-4 per group), 6 weeks of age, unless otherwise specified. The animals were allowed a minimum of 24 hours to acclimatize to the laboratory facility before the initiation of each experiment. Animals were identified by ear punch. The mice were not restricted by diet or activity during the experiments. The light/dark cycle was 12 hours, between 6 pm to 6 am. Controls were age- and sex-matched (n=3-4) animals. Mice were injected subcutaneously, twice a day (b.i.d.), with 2.5 µg peptide in a total volume of 0.5 cc of PBS and were monitored daily in the laboratory facility. Animals were sacrificed 10 or 14 days after injection, and were fasted at least 20 hours before sacrifice.

The mice were anaesthetised with $CO_2$ and exsanguinated by cardiac puncture. Blood was collected in 75 µl of TED (Trasysol; EDTA (5000 KIU/ml: 1.2 mg/ml; Diprotin-A), and the blood was centrifuged at 14 k×g for 5 minutes and the plasma was stored at −70 prior to analysis. The small bowel was removed from the peritoneal cavity, from pylorus to cecum, cleaned weighed and measured. For comparative purpose, sections from each animal were obtained from the identical anatomical position. Fragments each measuring 1.5-2.0 cm in length were obtained 8±2 cm, 18±2 cm, 32±2 cm from pylorus for histomorphometry representing proximal jejunum, distal jejunum and distal ileum. Each small bowel fragment was opened longitudinally on its antimesenteric border in a tissue block and then placed on 10% formalin (vol./vol.) overnight, then transferred to 70% ETOH.

Percentage change in small bowel weight was calculated by dividing the mean change in bowel weight of analog treated mice, relative to mice treated with vehicle only, by the mean bowel weight of mice treated with vehicle only, and multiplying this figure by 100.

Results of intestinotrophic activity assessment are shown in Table 1

TABLE 1

| # | GLP-2 analog (1-33 unless noted) | % Increase in small bowel weight |
|---|---|---|
| 1 | rGLP-2 | 45 |
| 2 | [Tyr$^1$]rGLP-2 | 37 |
| 3 | [D-Ala$^2$]rGLP-2 | 86 |
| 4 | [Gly$^2$]rGLP-2 | 70 |
| 5 | [Val$^2$]rGLP-2 | 65 |
| 6 | [Gly$^2$]hGLP-2 | 59 |
| 7 | [Gly$^2$Ala$^{20}$]hGLP-2 | 46 |
| 8 | [Gly$^2$Ala$^{10}$]hGLP-2 | 33 |
| 9 | [Ala$^1$Gly$^2$]hGLP-2 | 23 |
| 10 | [Gly$^2$Ala$^3$]hGLP-2 | 18 |
| 11 | [Gly$^2$Ala$^4$]hGLP-2 | 36 |
| 12 | [Glu$^3$]rGLP-2 | 33 |
| 13 | [Ala$^4$]rGLP-2 | 30 |
| 14 | [Tyr$^9$Ser$^{10}$Lys$^{11}$Tyr$^{12}$(desIle$^{13}$)]hGLP-2 | 41 |
| 15 | [Leu$^{10}$]rGLP-2 | 26 |
| 16 | [Nleu$^{10}$]rGLP-2 | 52 |
| 17 | [Met SO$_2$$^{10}$]rGLP-2 | 8 |
| 18 | [Lys$^{20}$]rGLP-2 | 62 |
| 19 | [Val$^{23}$Gln$^{24}$]hGLP-2 | 36 |
| 20 | Amidated C-term | 23 |
| 21 | [Gly$^2$Ala$^{24}$]hGLP-2 | 67 |
| 22 | [Gly$^2$Ala$^8$]hGLP-2 | 33 |
| 23 | [Gly$^2$Ala$^{11}$]hGLP-2 | 42 |
| 24 | [Gly$^2$Ala$^{21}$]hGLP-2 | 35 |
| 25 | [Gly$^2$Ala$^9$]hGLP-2 | 31 |
| 26 | [Gly$^2$Ala$^{16}$]hGLP-2 | 36 |
| 27 | [Gly$^2$Ala$^{17}$]hGLP-2 | 36 |
| 28 | [Gly$^2$Ala$^{28}$]hGLP-2 | 31 |
| 29 | [Gly$^2$Ala$^5$]hGLP-2 | 38 |
| 30 | [Gly$^2$Ala$^{31}$]hGLP-2 | 28 |
| 31 | [Gly$^2$Ala$^{27}$]hGLP-2 | 22 |

TABLE 1-continued

| # | GLP-2 analog (1-33 unless noted) | % Increase in small bowel weight |
|---|---|---|
| 32 | [Gly$^2$Ala$^{12}$]hGLP-2 | 18 |
| 33 | [Gly$^2$Ala$^{13}$]hGLP-2 | 18 |
| 34 | [Gly$^2$Ala$^7$]hGLP-2 | 22 |
| 35 | [Gly$^2$Ala$^6$]hGLP-2 | 18 |

It can be readily seen from the above table that analogs of mammalian GLP-2 molecules can have enhanced intestinotrophic activity. Furthermore, it is clear that depending on the substitution made, various levels of intestinotrophic activity are manifest. For example, [Gly$^2$]rGLP-2 has a greatly enhanced intestinotrphic activity compared to the naturally occurring molecule; [Gly$^2$]hGLP-2 has a substantially increased intestinotrophic activity compared with rGLP-2 and [Leu$^{10}$]rGLP-2 has less than a 50% increase in intestinotrophic activity.

The following experiments were conducted to confirm that the increase in bowel weight seen in experimental animals treated with DPP-IV resistant analogs of GLP-2, compared with animals treated with wild-type GLP-2, was attributable in part to the DPP-IV resistant nature of the molecules. This experiment took advantage of the availability of a DPP-IV deficient rat strain, Fisher 334 DPP-IV-rats. The effect of rGLP-2 injections on small bowel weight in the Fisher DPP-IV deficient rats was compared to that in normal Sprague-Dawley rats.

In the following experiments the Sprague-Dawley rats were injected s.c. twice daily with rGLP-2 in the Gelatin formulation. The Fisher rats were injected s.c. twice daily with GLP-2 peptides (both rGLP-2, and rGLP-2 analogs) in PBS.

Normal Sprague-Dawley rats treated with rGLP-2, 2.5 µg b.i.d. or 25 µg b.i.d., showed no % change in small bowel weight compared to control animals given vehicle alone. However, Fisher 334 DPP-IV-rats (DPP-IV deficient animals) demonstrated approximately a 40-50% increase in % change in small bowel weight when treated with 20 µg b.i.d. rGLP-2 compared to animals treated with vehicle only. Moreover, DPP-IV deficient animals treated with 20 µg [Gly$^2$] rGLP-2 showed a 50-60% increase in % change in small bowel weight compared with animals given vector alone. Further, Fisher 344 wild-type rats showed 75-85% increase in small bowel weight, over control animals given vehicle alone, when treated with 20 µg b.i.d. of [Gly$^2$]rGLP-2.

The above results strongly indicate that GLP-2 is inactivated in vivo in normal rats by cleavage of the two N-terminal residues by a DPP-IV-like enzyme. Furthermore, these results demonstrate that a GLP-2 analog modified so as to be resistant to cleavage by DPP-IV caused a substantial increase in bowel weight in normal rats, presumably as a result of increased GPL-2 half-life in vivo.

As the DPP-IV cleavage site is conserved in all known naturally occurring forms of GLP-2 it seems likely that in mammals DPP-IV cleavage is an important, and probably the primary mechanism whereby GLP-2 is inactivated in vivo. Importantly, GLP-2 analogs resistant to DPP-TV cleavage have enhanced intestinotrophic activity compared to native form.

Example 5

Experiments assessing the small bowel inducing activity of various analogs was repeated as described above for Example 4. In these experiments, the small bowel inducing activity of each analog in mice was calculated relative to that of native rat GLP-2 (1-33) (expressed as 100% of activity). Resistance of analogs to DPP-IV cleavage was performed as described above in Example 3. Results are tabulated below in Table 2.

TABLE 2

| Identification | Description of Sequence ALE-0109 | % Activity Rel. to rGLP-2 | % Cleaved by DPP-IV |
|---|---|---|---|
| ratGLP-2(1-33) | Native rat sequence | 100% | 58% |
| ratGLP-2(4-33) | N-3; 3 N-terminal res. removed | 6% | |
| Ac-ratGLP-2(1-33) | N-Acetyl | 44% | 0% |
| anglerfish GLP-1 | Native anglerfish GLP-2 | 7% | |
| [Arg-1]ratGLP-2(-1-33) | Arg added to N-terminus | 11% | 0% |
| ratGLP-2(1-30) | C-3; 3 C-terminal res. removed | 23% | |
| ratGLP-2(1-25) | C-8; 8 C-terminal res. removed | 8% | |
| ratGLP-2(1-33)amide | C-terminal amide | 56% | |
| [Arg-2,Arg-1]ratGLP-2(2-33) | Arg-Arg added to N-terminus | 43% | 0% |
| [DAla2]ratGLP-2(1-33) | Ala2->D-Ala2 | 210% | 0% |
| [Gly2]ratGLP-2(1-33) | Ala2->Gly2 | 196% | 0% |
| [Tyr1]ratGLP-2(1-33) | His1->Tyr1 | 81% | 100% |
| [Ala4]ratGLP-2(1-33) | Gly4->Ala4 | 59% | 72% |
| [Glu3]ratGLP-2(1-33) | Asp3->Glu3 | 65% | 50% |
| [Leu10]ratGLP-2(1-33) | Met10->Leu10 | 51% | |
| [Nle10]ratGLP-2(1-33) | Met10->Nle10 | 100% | |
| [Lys20]ratGLP-2(1-33) | Arg20->Lys20 | 120% | |
| [Ser2,Gln3]hGLP-2(1-33) | Ala2->Ser2, Asp3->Glu3 | 11% | 0% |
| [Val23,Gln24]hGLP-2(1-33) | Ile23->Val23, Asn24->Gln24 | 82% | |
| [Val2]GLP-2(1-33) | Ala2->Val2, TFA | 145% | 0% |
| Degu GLP-2 | Native degu sequence | 70% | |
| [Tyr9,Ser10,Lys11,Tyr12, des-Ile13]hGLP-2(1-33) | Glu9->Tyr9, Met10->Ser10, Asn11->Lys11, Thr12->Tyr12, and deletion of Ile13 | 94% | |
| [Gly2,Ala8]hGLP-2(1-33) | Ala2->Gly2, Asp8->Ala8 | 120% | |
| [Gly2,Ala11]hGLP-2(1-33) | Ala2->Gly2, Asn11->Ala11 | 150% | |
| [Gly2,Ala21]hGLP-2(1-33) | Ala2->Gly2, Asp21->Ala21 | 125% | |
| [Gly2,Ala24]hGLP-2(1-33) | Ala2->Gly2, Asn24->Ala24 | 139% | 0% |
| [Gly2,Ala25]hGLP-2(1-33) | Ala2->Gly2, Trp25->Ala25 | 18% | |
| [Gly2,Ala26]hGLP-2(1-33) | Ala2->Gly2, Leu26->Ala26 | 28% | |
| [Gly2,Ala27]hGLP-2(1-33) | Ala2->Gly2, Ile27->Ala27 | 82% | |
| [Gly2,Ala9]hGLP-2(1-33) | Ala2->Gly2, Glu9->Ala9 | 112% | |
| [Gly2,Ala10]hGLP-2(1-33) | Ala2->Gly2, Met10->Ala10 | 82% | |
| [Gly2,Ala12]hGLP-2(1-33) | Ala2->Gly2, Thr12->Ala12 | 67% | |
| [Gly2,Ala13]hGLP-2(1-33) | Ala2->Gly2, Ile13->Ala13 | 67% | |
| [Gly2,Ala14]hGLP-2(1-33) | Ala2->Gly2, Leu14->Ala14 | 30% | |
| [Gly2,Ala16]hGLP-2(1-33) | Ala2->Gly2, Asn16->Ala16 | 130% | |
| [Gly2,Ala17]hGLP-2(1-33) | Ala2->Gly2, Leu17->Ala17 | 130% | |
| [Gly2,Ala20]hGLP-2(1-33) | Ala2->Gly2, Arg20->Ala20 | 105% | |
| [Gly2,Ala23]hGLP-2(1-33) | Ala2->Gly2, Ile23->Ala23 | 24% | |
| [Gly2,Ala28]hGLP-2(1-33) | Ala2->Gly2, Gln28->Ala28 | 130% | |
| [Gly2,Ala30]hGLP-2(1-33) | Ala2->Gly2, Lys30->Ala30 | 24% | |
| [Gly2,Ala31]hGLP-2(1-33) | Ala2->Gly2, Ile31->Ala31 | 100% | |
| [Gly2]hGLP-2(1-33) | Ala2->Gly2 | 300% | 0% |
| [Ala1,Gly2]hGLP-2(1-33) | His1->Ala1, Ala2->Gly2 | 53% | 0% |
| [Gly2,Ala3]hGLP-2(1-33) | Ala2->Gly2, Asp3->Ala3 | 44% | 0% |
| [Gly2,Ala4]hGLP-2(1-33) | Ala2->Gly2, Gly4->Ala4 | 100% | 0% |
| [Gly2,Ala5]hGLP-2(1-33) | Ala2->Gly2, Ser5->Ala5 | 136% | 0% |
| [Gly2,Ala6]hGLP-2(1-33) | Ala2->Gly2, Phe6->Ala6 | 67% | |
| [Gly2,Ala7]hGLP-2(1-33) | Ala2->Gly2, Ser7->Ala7 | 82% | |
| [Pro1]hGLP-2(1-33) | His1->Pro1 | 12% | 0% |
| [Met(O)10]ratGLP-2(1-33) | Met10 sulfoxide | 18% | |
| [Gln20]hGLP-2(1-33) | Arg20->Gln20 | 80% | |
| [Asp1]hGLP-2(1-33) | His1->Asp1 | 60% | 0% |
| [tBuGly2]hGLP-2 | Ala2->t-butyl-Gly2 | 123% | 0% |
| [Tyr34]hGLP-2(1-34) | Addition of C-terminal Tyr | 135% | |
| [Asp2]hGLP-2(1-33) | Ala2->Asp2 | 83% | 0% |
| [Glu2]hGLP-2(1-33) | Ala2->Glu2 | 93% | 0% |
| [Phe2]hGLP-2(1-33) | Ala2->Phe2 | 50% | 0% |
| [His2]hGLP-2(1-33) | Ala2->His2 | 0% | 0% |
| [Ile2]hGLP-2(1-33) | Ala2->Ile2 | 90% | 0% |
| [Lys2]hGLP-2(1-33) | Ala2->Lys2 | 90% | 0% |
| [Met2]hGLP-2(1-33) | Ala2->Met2 | 170% | 0% |
| [Asn2]hGLP-2(1-33) | Ala2->Asn2 | 67% | 0% |
| [Pro2]hGLP-2(1-33) | Ala2->Pro2 | 50% | 16% |
| [Gln2]hGLP-2(1-33) | Ala2->Gln2 | 100% | 0% |
| [Ser2]hGLP-2(1-33) | Ala2->Ser2 | 167% | 0% |
| [Thr2]hGLP-2(1-33) | Ala2->Thr2 | 117% | 0% |
| [Val2]hGLP-2(1-33) | Ala2->Val2 | 180% | 13% |
| [Tyr2]hGLP-2(1-33) | Ala2->Tyr2 | 57% | 0% |

TABLE 2-continued

| Identification | Description of Sequence ALE-0109 | % Activity Rel. to rGLP-2 | % Cleaved by DPP-IV |
|---|---|---|---|
| [D-Ala2]hGLP-2(1-33) | Ala2->D-Ala2 | 130% | 0% |
| hGLP-2(1-33) | Native human sequence | 100% | 60% |
| [desNH2Tyr1]hGLP-2(1-33) | His1->desamino-Tyr1 | 125% | 15% |
| [Thr5]hGLP-2(1-33) | Ser5->Thr5 | 73% | |
| [Ser16,Arg17,Arg18] hGLP-2(1-33) | Asn16->Ser16, Leu17->Arg17, Ala18->Arg18 | 59% | |
| [Asn33]hGLP-2(1-33) | Asp33->Asn33 | 91% | |
| [Pen2]hGLP-2(1-33) | Ala2->L-penicillamine2 | 58% | 20% |
| [bAla2]hGLP-2(1-33) | Ala2->beta-Ala2 | 118% | 0% |
| [aAbu2]hGLP-2(1-33) | Ala2->alpha-aminobutyric acid2 | 84% | 49% |
| [Nval2]hGLP-2(1-33) | Ala2->Nval2 (norvaline) | 111% | 0% |
| [PhGly2]hGLP-2(1-33) | Ala2->L-phenyl-Gly2 | 37% | 0% |
| [Agm34]hGLP-2(1-34) | Addition of C-terminal agmatine (Agm is des-COOH Arg) | 97% | |
| [Arg30]hGLP-2(1-33) | Lys30->Arg30 | 103% | 59% |
| [Pro3]hGLP-2(1-33) | Asp3->Pro3 | 140% | 0% |
| [Ala5, Ala7]hGLP-2(1-33) | Ser5->Ala5, Ser7->Ala7 | 108% | 77% |
| [Tyr1, Gly2]hGLP-2(1-33) | His1->Tyr1, Ala2->Gly2 | 241% | 0% |
| [Glu33]hGLP-2(1-33) | Asp33->Glu33 | 121% | 55% |
| [Phe25]hGLP-2(1-33) | Trp25->Phe25 | 114% | 54% |
| [Tyr25]hGLP-2(1-33) | Trp25->Tyr25 | 64% | 48% |
| [Gly2, Tyr34]hGLP-2(1-34) | Ala2->Gly2 + C-terminal Tyr | 297% | 0% |
| [Aib2]hGLP-2(1-33) | Ala2->aminoisobutyric acid2 | 202% | 0% |
| [Gly2, Arg34]hGLP-2(1-34) | Ala2->Gly2 + C-terminal Arg | ~250% | 0% |

EQUIVALENTS

The foregoing written specification is sufficient to enable one skilled in the art to practice the invention. Indeed, various modifications of the above-described means for carrying out the invention which are obvious to those skilled in the field of molecular biology, protein chemistry, medicine or related fields are intended to be within the scope of the following claims.

What is claimed is:

1. An intestinotrophic GLP-2 analog of SEQ ID NO: 2, wherein at least one amino acid at one or more positions selected from the group consisting of positions 1, 5, 7, 16-18, 25, and 33 is substituted with an amino acid other than a wild type, mammalian GLP-2 residue; wherein positions 2-4, 6, 8-15, 19-24, and 26-32 are unmodified, and wherein 4 to 8 residues are optionally deleted from the C-terminus of SEQ ID NO: 2.

2. The GLP-2 analog according to claim 1, wherein said analog incorporates at least one amino acid substitution selected from the group consisting of:
   a) incorporation of Pro, Asp, or desNH$_2$Tyr at position 1;
   b) incorporation of Thr or Ala at position 5;
   c) incorporation of Ala at position 7;
   d) incorporation of Ser at position 16;
   e) incorporation of Arg at position 17;
   f) incorporation of Arg at position 18;
   g) incorporation of Phe or Tyr at position 25; and
   h) incorporation of Glu at position 33.

3. The GLP-2 analog according to claim 1 selected from the group consisting of: [Pro$^1$]hGLP-2(1-33); [Asp$^1$]hGLP-2 (1-33); [desNH$_2$Tyr$^1$]hGLP-2 (1-33); [Thr$^5$]hGLP-2 (1-33); [Ser$^{16}$, Arg$^{17}$, Arg$^{18}$]hGLP-2 (1-33); [Ala$^5$, Ala$^7$]hGLP-2 (1-33); [Glu$^{33}$]hGLP-2 (1-33); [Phe$^{25}$]hGLP-2 (1-33); [Tyr$^{25}$]hGLP-2 (1-33).

4. A pharmaceutical composition comprising a therapeutically effective amount of a GLP-2 analog according to claim 1 and a pharmaceutically acceptable carrier.

5. A method for promoting growth of small bowel tissue in patient in need thereof, comprising the step of delivering to the patient the pharmaceutical composition of claim 4.

6. A method for treating a gastrointestinal disease, wherein the method comprises administering to a patient having the gastrointestinal disease a therapeutically effective amount of a GLP-2 analog according to claim 1, together with a pharmaceutically acceptable carrier to reduce a pathological effect or symptom of the gastrointestinal disease.

7. The method of claim 6, wherein the gastrointestinal disease is selected from the group consisting of ulcers, digestion disorders, malabsorption syndromes, short-gut syndrome, cul-de-sac syndrome, inflammatory bowel disease, celiac sprue, tropical sprue, hypogammaglobulinemic sprue, enteritis, regional enteritis (Crohn's disease), small intestinal damage due to toxic or other chemotherapeutic agents, and short bowel syndrome.

8. A method for promoting growth of small bowel tissue in a patient in need thereof, comprising the step of delivering to the patient a pharmaceutical composition comprising a therapeutically effective amount of a GLP-2 analog according to claim 3.

9. A method for treating a gastrointestinal disease, wherein the method comprises administering to a patient having the gastrointestinal disease a therapeutically effective amount of a GLP-2 analog according to claim 3 together with a pharmaceutically acceptable carrier to reduce a pathological effect or symptom of the gastrointestinal disease.

10. The method of claim 9, wherein the gastrointestinal disease is selected from the group consisting of ulcers, digestion disorders, malabsorption syndromes, short-gut syndrome, cul-de-sac syndrome, inflammatory bowel disease, celiac sprue, tropical sprue, hypogammaglobulinemic sprue, enteritis, regional enteritis (Crohn's disease), small intestinal damage due to toxic or other chemotherapeutic agents, and short bowel syndrome.

11. A method of identifying intestinotrophic analogs of GLP-2, comprising the steps of:
   a. obtaining a GLP-2 analog according to claim 1;
   b. treating a mammal with said analog using a regimen capable of eliciting an intestinotrophic effect when utilized for rat GLP-2; and
   c. determining the effect of said analog on small bowel weight relative to a mock treated control mammal, whereby said intestinotrophic analog of GLP-2 is identified as an analog which elicits an increase in said weight.

12. A method for promoting growth of small bowel tissue in a patient in need thereof, comprising the step of delivering to the patient a pharmaceutical composition comprising the GLP-2 analog of claim 1.

13. The peptide [desNH$_2$Tyr$^1$]hGLP-2(1-33).

* * * * *

```
                       SEQUENCE LISTING

<160> NUMBER OF SEQ ID NOS: 4

<210> SEQ ID NO 1
<211> LENGTH: 37
<212> TYPE: PRT
<213> ORGANISM: Artificial Sequence
<220> FEATURE:
<223> OTHER INFORMATION: This sequence is a synthetically derived
      Glucagon-Like Peptide-2 analog. Amino acid substitutions may or
      may not represent those found in nature.
<220> FEATURE:
<221> NAME/KEY: MISC_FEATURE
<222> LOCATION: (1)..(1)
<223> OTHER INFORMATION: Xaa is a basic amino acid selected from the
      group Arg, Lys, and His. Xaa may or may not be present in the
      sequence. The substitution is synthetically designed.
<220> FEATURE:
<221> NAME/KEY: MISC_FEATURE
<222> LOCATION: (2)..(2)
<223> OTHER INFORMATION: Xaa is a basic amino acid selected from the
      group Arg, Lys, and His. Xaa may or may not be present in the
      sequence. The substitution is synthetically designed.
<220> FEATURE:
<221> NAME/KEY: MISC_FEATURE
<222> LOCATION: (3)..(3)
<223> OTHER INFORMATION: Xaa is His or Tyr. The substitution is
      synthetically designed.
<220> FEATURE:
<221> NAME/KEY: MISC_FEATURE
<222> LOCATION: (4)..(4)
<223> OTHER INFORMATION: Xaa is Ala or any amino acid conferring  on
      said analog resistance to DPP-IV enzyme. The substitution is
      synthetically designed.
<220> FEATURE:
<221> NAME/KEY: MISC_FEATURE
<222> LOCATION: (5)..(5)
<223> OTHER INFORMATION: Xaa is Pro, HPro, Asp, or Glu. The substitution
      is synthetically designed.
<220> FEATURE:
```

-continued

```
<221> NAME/KEY: MISC_FEATURE
<222> LOCATION: (6)..(6)
<223> OTHER INFORMATION: Xaa is Gly or Ala The substitution is
      synthetically designed.
<220> FEATURE:
<221> NAME/KEY: MISC_FEATURE
<222> LOCATION: (11)..(11)
<223> OTHER INFORMATION: Xaa is Glu or Tyr. The substitution is
      synthetically designed.
<220> FEATURE:
<221> NAME/KEY: MISC_FEATURE
<222> LOCATION: (12)..(12)
<223> OTHER INFORMATION: Xaa is Ser if position 11 is Tyr, otherwise Met
      or an oxidatively stable Met replacement amino acid. The
      substitution is synthetically designed.
<220> FEATURE:
<221> NAME/KEY: MISC_FEATURE
<222> LOCATION: (13)..(13)
<223> OTHER INFORMATION: Xaa is Lys if position 11 is Tyr, or Asn. The
      substitution is synthetically designed.
<220> FEATURE:
<221> NAME/KEY: MISC_FEATURE
<222> LOCATION: (14)..(14)
<223> OTHER INFORMATION: Xaa is Tyr if position 11 is Tyr, or Thr. The
      substitution is synthetically designed.
<220> FEATURE:
<221> NAME/KEY: MISC_FEATURE
<222> LOCATION: (15)..(15)
<223> OTHER INFORMATION: Xaa is Ile, or Xaa is not present if position
      11 is Tyr. The substitution is synthetically designed.
<220> FEATURE:
<221> NAME/KEY: MISC_FEATURE
<222> LOCATION: (21)..(21)
<223> OTHER INFORMATION: Xaa is Ala or Thr. The substitution is
      synthetically designed.
<220> FEATURE:
<221> NAME/KEY: MISC_FEATURE
<222> LOCATION: (22)..(22)
<223> OTHER INFORMATION: Xaa is Arg, Lys, His, or Ala. The substitution
      is synthetically designed.
<220> FEATURE:
<221> NAME/KEY: MISC_FEATURE
<222> LOCATION: (25)..(25)
<223> OTHER INFORMATION: Xaa is Ile or Val. The substitution is
      synthetically designed.
<220> FEATURE:
<221> NAME/KEY: MISC_FEATURE
<222> LOCATION: (26)..(26)
<223> OTHER INFORMATION: Xaa is Asn or Ala if position 25 is Ile. The
      substitution is synthetically designed.
<220> FEATURE:
<221> NAME/KEY: MISC_FEATURE
<222> LOCATION: (33)..(33)
<223> OTHER INFORMATION: Xaa is Ile. Xaa may or may not be present in
      the sequence. The substitution is synthetically designed.
<220> FEATURE:
<221> NAME/KEY: MISC_FEATURE
<222> LOCATION: (34)..(34)
<223> OTHER INFORMATION: Xaa is Thr if position 33 is Ile. Xaa may or
      may not be present in the sequence. The substitution is
      synthetically designed.
<220> FEATURE:
<221> NAME/KEY: MISC_FEATURE
<222> LOCATION: (35)..(35)
<223> OTHER INFORMATION: Xaa is Asp if position 34 is Thr.  Xaa may or
      may not be present in the sequence. The substitution is
      synthetically designed.
<220> FEATURE:
<221> NAME/KEY: MISC_FEATURE
<222> LOCATION: (36)..(36)
<223> OTHER INFORMATION: Xaa is a basic amino acid selected from the
      group Arg, Lys, and His. Xaa may or may not be present in the
      sequence.  The substitution is synthetically designed.
<220> FEATURE:
<221> NAME/KEY: MISC_FEATURE
<222> LOCATION: (37)..(37)
<223> OTHER INFORMATION: Xaa is a basic amino acid selected from the
      group Arg, Lys, and His. Xaa may or may not be present in the
      sequence. The substitution is synthetically designed.
```

```
<400> SEQUENCE: 1

Xaa Xaa Xaa Xaa Xaa Xaa Ser Phe Ser Asp Xaa Xaa Xaa Xaa Leu
1               5                   10                  15

Asp Asn Leu Ala Xaa Xaa Asp Phe Xaa Xaa Trp Leu Ile Gln Thr Lys
                20              25                  30

Xaa Xaa Xaa Xaa Xaa
        35

<210> SEQ ID NO 2
<211> LENGTH: 33
<212> TYPE: PRT
<213> ORGANISM: Homo sapiens

<400> SEQUENCE: 2

His Ala Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
                20              25                  30

Asp

<210> SEQ ID NO 3
<211> LENGTH: 5
<212> TYPE: PRT
<213> ORGANISM: Artificial Sequence
<220> FEATURE:
<223> OTHER INFORMATION: This sequence is synthetically derived and may
      be inserted into a Glucagon-Like Peptide-2 analog.
<220> FEATURE:
<221> NAME/KEY: MISC_FEATURE
<222> LOCATION: (2)..(2)
<223> OTHER INFORMATION: Xaa is Met or an oxidatively stable Met-
      replacement amino acid. The substitution is synthetically
      designed.

<400> SEQUENCE: 3

Glu Xaa Asn Thr Ile
1               5

<210> SEQ ID NO 4
<211> LENGTH: 4
<212> TYPE: PRT
<213> ORGANISM: Artificial Sequence
<220> FEATURE:
<223> OTHER INFORMATION: This sequence is synthetically derived and may
      be inserted into a Glucagon-Like Peptide-2 analog.

<400> SEQUENCE: 4

Tyr Ser Lys Tyr
1
```